US005776891A

United States Patent [19]
Coon et al.

[11] Patent Number: 5,776,891
[45] Date of Patent: Jul. 7, 1998

[54] COMPOSITIONS FOR REDUCING MULTIDRUG RESISTANCE

[75] Inventors: John S. Coon, Oak Park, Ill.; Mannarsamy Balasubramanian, Roswell, Ga.; R. Martin Emanuele, Alpharetta, Ga.; Himanshu Shah, Atlanta, Ga.

[73] Assignee: Rush Prebyterian-St. Luke Medical Center, Chicago, Ill.

[21] Appl. No.: 480,582

[22] Filed: Jun. 7, 1995

Related U.S. Application Data

[60] Division of Ser. No. 445,191, May 19, 1995, abandoned, which is a continuation-in-part of Ser. No. 246,037, May 19, 1994, abandoned, which is a continuation-in-part of Ser. No. 982,766, Dec. 7, 1992, abandoned, which is a continuation-in-part of Ser. No. 805,186, Dec. 10, 1991, abandoned.

[51] Int. Cl.$^6$ .......................... A61K 38/16; A01N 43/04
[52] U.S. Cl. ........................ 514/10; 514/34; 514/35; 514/183; 514/283; 514/411; 514/506; 514/515; 514/765; 514/950
[58] Field of Search ................... 514/10, 34, 35, 514/183, 283, 411, 506, 515, 765, 950; 525/92 A, 174, 177, 133.5

[56] References Cited

U.S. PATENT DOCUMENTS

| | | | |
|---|---|---|---|
| 3,919,411 | 11/1975 | Glass et al. . | |
| 4,282,054 | 8/1981 | Mattor et al. | 156/289 |
| 4,557,934 | 12/1985 | Cooper . | |
| 4,563,351 | 1/1986 | Caslavsky et al. . | |
| 4,634,732 | 1/1987 | Miller et al. | 524/504 |
| 4,753,965 | 6/1988 | Stemerick et al. . | |
| 4,803,081 | 2/1989 | Falk et al. . | |
| 4,863,968 | 9/1989 | Edwards et al. . | |
| 4,889,525 | 12/1989 | Yuhas et al. . | |
| 4,904,697 | 2/1990 | Sunkara et al. . | |
| 4,923,862 | 5/1990 | Hirota . | |
| 4,978,332 | 12/1990 | Luck et al. . | |
| 4,978,622 | 12/1990 | Mishell et al. . | |
| 4,996,321 | 2/1991 | Baldwin . | |
| 5,108,989 | 4/1992 | Amento et al. . | |

FOREIGN PATENT DOCUMENTS

WO 93/11668  6/1993  WIPO .

OTHER PUBLICATIONS

Paradis, R. et al., "Use of pluronic micelles to overcome multidrug resistance," *International Journal of Oncology*, 5:1305–1308 (1994).

Pages, M. et al., "Elimination of P–170 Mediated Multi-Drug Resistance by Solubilization in Pluronic Micelles," *Database BIOSIS*, Philadelphia, PA (1992) and *Proc. Am. Assoc. Cancer Res. Ann. Meet.*, 33: 552 (1992).

Buckingham, L.E. et al., "Comparison of Solutol HS 15, Cremophor EL and novel ethoxylated fatty acid surfactants as multidrug resistance modification agents," *Int. J. Cancer*, 62(4):436–442 (1995).

Chong, A.S. et al. "Diverse multidrug–resistance–modification agents inhibit cytolytic activity of natural killer cells," *Cancer Immunol. Immunother.*, 36(2):133–139 (1993).

Coon, et al., "SOLUTOL® HS15, nontoxic polyoxyethylene esters of 12–hydroxystearic acid, reverses multidrug resistance," *Cancer Research*, vol. 15, pp. 897–902 (Feb. 1991).

Coon, J.S., et al., "Survey of surfactants for reversing multidrug resistance," *Proc. Am. Assoc. Cancer Res. Annu. Meet.*, vol. 33, p. 484 (Mar. 1992).

Woodcock, D., et al., "Reversal of the Multidrug Resistance Phenotype with Cremophor EL, a Common Vehicle for Water–insoluble Vitamins and Drugs," *Cancer Research*, vol. 50, pp. 4199–4230 (Jul. 15, 1990).

Riehm, H., et al., "Potentiation of Drug Effect by Tween 80 in Chinese Hamster Cells Resistant to Actinomycin D. and Daunomycin," *Cancer Research*, vol. 32, pp. 1195–1200(Jun. 1972).

Woodcock, D., et al., "Reversal of Multidrug resistance by surfactants," *Br. J. Cancer*, vol. 66, pp. 62–88 (Jul. 1992).

Endicott, J., et al., "The Biochemistry of P–Glycoprotein–Mediated Multidrug Resistance," *Annu. Rev. Biochem.*, vol. 58, pp. 137–171 (1989).

Pastan, I., et al., "Molecular Manipulations of the Multidrug Transporter: A New Role for Transgenic Mice," *FASEB Journal*, vol. 5, pp. 2523–2528 (1991).

Drug & Market Development, "Multidrug Resistance in Cancer Therapy," *Drug & Market Development*, vol. 3, No. 1/2 (Jul. 6, 1992).

Cornwell, M., et al., "Membrane Vesicles from Multidrug–Resistant Human Cancer Cells Contain a Specific 150–to 170–kDA Protein Detected by Photoaffinity Labeling," *Proc. Natl. Acad. Sci., USA*, vol. 83, pp. 3847–3850 (1986).

Sehested, M., et al., "Relationship of VP–16 to the Classical Multidrug Resistance Phenotype," *Cancer Research*, vol. 52, pp. 2874–2879 (May 15, 1992).

Chen, C., et al., "Internal Duplication and Homology with Bacterial Transport Proteins in the MDR1 (P–Glycoprotein) Gene from Multidrug–Resistant Human Cells," *Cell*, vol. 47, pp. 381–389 (1986).

(List continued on next page.)

*Primary Examiner*—Nathan M. Nutter
*Attorney, Agent, or Firm*—Jones & Askew

[57] ABSTRACT

The present invention comprises methods and compositions for reducing or eliminating multidrug resistance in cancers or certain infections by drug resistant microorganisms in patients. According to the method and composition of the present invention, a non-ionic amphipathic diester of fatty acids or a reverse poloxmer is administered to a patient in which a cancer or microorganism exhibits multidrug resistance to the chemotherapeutic agent. The method and composition of the present invention may be employed with particular efficacy where multidrug resistance to any chemotherapeutic agent has been conferred upon a cancer.

3 Claims, 15 Drawing Sheets

OTHER PUBLICATIONS

Kartner, N., et al., "Detection of P–Glycoprotein in Mutidrug–Resistant Cell Lines by Monoclonal Antibodies," *Nature*, vol. 316, pp. 820–823 (1985).

Beck, W., et al., "Altered Surface Membrane Glycoproteins in Vinca Alkoloid–resistant Human Leukemic Lymphoblasts," *Cancer Research*, vol. 39, pp. 2070–2076 (1979).

Gerlack, J., et al., "Homology Between P–Glycoprotein and a Bacterial Haemolysin Transport Protein Suggess a Model for Multidrug Resistant," *Nature*, vol. 324, pp. 485–489 (1986).

Willingham, M., et al., "Immunocytochemical Localization of P170 at the Plasma Membrane of Multidrug–Resistant Human Cells," *Journal of Histochemistry and Cytochemistry*, vol. 35, No. 12, pp. 1451–1456 (1987).

Hamada, H., et al., "Purification of the 170–to 180–Kilodalton Membrane Glycoprotein Associated with Multidrug Resistance," *Journal of Biological Chemistry*, vol. 263, No. 3, pp. 1454–1458 (1988).

Juliano, R., et al., "A Surface Glycoprotein Modulating Drug Permeability in Chinese Hamster Ovary Cell Mutants," *Biochemica et Biophysica Acta*, vol. 455, pp. 152–162 (1976).

Shen, D., et al., "Multiple Drug–Resistant Human KB Carcinoma Cells Independently Selected for High–Level Resistance to Colchicine, Adriamycin, or Vinblastine Show Changes in Expression of Specific Proteins," *Journal of Biological Chemistry*, vol. 261, No. 17, pp. 7762–7770 (1986).

Dordal, M., et al., "Kinetic Analysis of P–Glycoprotein–Mediated Doxorubicin Efflux," *The Journal of Pharmacology and Experimental Theerapeutics*, vol. 263, pp. 752–766 (Nov. 1992).

Goldstein, L., et al., "Expression of a Multidrug Resistance Gene in Human Cancers," *Journal of the National Cancer Institute*, vol. 81, No. 2, pp. 116–124 (1989).

Gros, P., et al., "Mammalian Multidrug Resistance Gene: Complete cDNA Sequence Indicates Strong Homology to Bacterial Transport Proteins," *Cell*, vol. 47, pp. 371–380 (1986).

Roninson, I., et al., Amplification of Specific DNA Sequences Correlates with Multi–drug Resistance in Chinese Hamster Cells, *Nature*, vol. 309, pp. 626–628 (1984).

Thorgeirsson, S., et al., "Expression of the Multidrug–Resistant Gene in Hepatocarcinogenesis and Regenerating Rat Liver," *Science*, vol. 236, pp. 1120–1122 (1987).

Scotto, K., et al., "Amplifications and Expression of Genes Associated with Multidrug Resistance in Mammalian Cells," *Science*, vol. 232, pp. 751–755 (May 9, 1986).

Van der Bliek, A., et al., "Overexpression and Amplification of Five Genes in a Multidrug–Resistant Chinese Hamster Ovary Cell Line," *Molecular and Cellular Biology*, vol. 6, No. 5, pp. 1671–1678 (1986).

Gros, P., et al., "Isolation and Expression of a Complementary DNA that Confers Multidrug Resistance," *Nature*, vol. 323, pp. 728–732 (1986).

Fojo, A., et al., "Intrinsic Drug Resistance in Human Kidney Cancer is Associated with Expression of a Human Multidrug–Resistance Gene," *Journal of Clinical Oncology*, vol. 5, No. 12, pp. 1922–1927 (1987).

Roninson, I., et al., "Isolation of Human mdr DNA Sequences Amplified in Multidrug–Resistant KB Carcinoma Cells," *Proc. Natl. Acad. Sci., USA*, vol. 83, pp. 4538–4542 (1986).

Fojo, A., et al., "Amplification of DNA Sequences in Human Multidrug–Resistant KB Carcinoma Cells," *Proc. Natl. Acad. Sci. USA*, vol. 82, pp. 7661–7665 (1985).

Ueda, K., et al., "The Human Multidrug Resistant (mdrl) Gene," *Journal of Biological Chemistry*, vol. 262, pp. 505–508 (1987).

Arceci, R., et al., "The Gene Encoding Multidrug Resistance is Induced and Expressed at high Levels During Pregnancy in the Secretory Epithelium of the Uterus," *Proc. Natl., Acad. Sci., USA*, vol. 85, pp. 4350–4354 (1988).

Fojo, A., et al., "Expression of a Multidrug–resistance Gene in Human Tumors and Tissues," *Proc. Natl. Acad. Sci., USA*, vol. 84, pp. 265–269 (1987).

Mukhopadhyay, T., et al., "Expression of the mdr (P–Glycoprotein) Gene in Chinese Hamster Digestive Tracts," *Journal of the National Cancer Institute*, vol. 80, No. 4, pp. 269–275 (1988).

Shen, D., et al., "Human Multidrug–Resistant Cell Lines: Increased mdrl Expression Can Precede Gene Amplification," *Science*, vol. 232, pp. 643–645 (1986).

Fairchild, C., et al., "Carcinogen–Induced mdr Overexpression is Associated with Xenobiotic Resistance in Rat Preneoplastic Liver Nodules and Hepatocellular Carcinomas," *Proc. Natl. Acad. Sci., USA*, vol. 84, pp. 7701–7705 (1987).

Cole, S., et al., "Overexpression of a Transporter Gene in a Multidrug–Resistant Human Lung Cancer Cell Line," *Science*, vol. 258, pp. 1650–1654 (Dec. 4, 1992).

Ling, V., et al., "Reduced Permeability in CHO Cells as a Mechanism of Resistance to Colchinine," *J. Cell. Physiol.*, vol. 83, pp. 103–116 (1974).

Akiyama, S., et al., "Isolation and Genetic Characterization of Human KB Cell Lines Resistant to Multiple Drugs," *Somatic Cell and Molecular Genetics*, vol. 11, No. 1, pp. 117–126 (1985).

Bhalla, K., et al., "Isolation and Characterization of an Anthracycline–Resistant Human Leukemic Cell Line," *Cancer Research*, vol. 45, pp. 3657–3662 (1985).

Fojo, A., et al., "Reduced Drug Accumulation in Multiple Drug–Resistant Human KB Carcinoma Cell Lines," *Cancer Research*, vol. 45, pp. 3002–3007 (1985).

Skovsgaard, T., "Mechanism of Cross–Resistance between Vincristin and Daunorubicin in Ehrlich Ascites Tumor Cells," *Cancer Research*, vol. 38, pp. 4722–4727 (1978).

FitzGerald, D., et al., "A Monoclonal Antibody–Pseudomonas Toxin Conjugate that Specifically Kills Multidrug–Resistant Cells," *Proc. Natl. Acad. Sci., USA*, vol. 84, pp. 4288–4292 (1987).

Micklisch, G., et al., "Transgenic Mice the Express the Human Multidrug–Resistance Gene in Bone Marrow Enable a Rapid Identification of Agents that Reverse Drug Resistance," *Proc. Natl. Acad. Sci., USA*, vol. 88, pp. 547–551 (1991).

Lelong, I., et al., "Fluorescent Verpamil Derivative for Monitoring Activity of the Multidrug Transporter," *Molecular Pharmacology*, vol. 40, pp. 490–494 (1991).

Efferth, T., et al., "Reciprocal Correlation Between Expression of P–Glycoprotein and Accumulation of Rhodamine 123 in Human Tumors," *Anticancer Res.*, vol. 9, pp. 1633–1638 (1989).

Neyfakh, A.A., et al., "Use of Fluorescent Dyes as Molecular Probes for the Study of Multidrug Resistance," *Exp. Cell Res.*, vol. 174, pp. 168–176 (1988).

FIG_1

5,776,891

COMPOSITIONS FOR REDUCING MULTIDRUG RESISTANCE

CROSS-REFERENCE TO RELATED APPLICATIONS

This patent application is a divisional application of U.S. patent application Ser. No. 08/445,191, which was filed on May 19, 1995 and now abandoned which is a continuation in part of U.S. patent aplication Ser. No. 08/246,037 which was filed on May 19, 1994 and, now abandoned, and which is a continuation-in-part of U.S. patent application Ser. No. 07/982,766, filed Dec. 7, 1992, and now abandoned, and which is a continuation-in-part of U.S. patent application Ser. No. 07/805,186, filed Dec. 10, 1991, now abandoned, all of which are incorporated herein by reference.

TECHNICAL FIELD

The present invention relates to the use of resistance modification agents in vivo to reverse multidrug resistance in human or animal cells and in drug resistant microorganisms. More particularly, the present invention comprises polyethylene glycol polymers with either fatty acids or block polypropylene glycol on both ends of the polyethylene glycol polymer. These compositions are capable of reducing multidrug resistance in vivo.

BACKGROUND OF THE INVENTION

One of the major problems of cancer chemotherapy is the existence of drug resistance in tumors resulting in reduced responsiveness to chemotherapy. Some human cancers, e.g. kidney and colon carcinoma, are drug resistant before treatment begins, while in others drug resistance develops over successive rounds of chemotherapy. One type of drug resistance, called multidrug resistance, is characterized by cross resistance to functionally and structurally unrelated drugs. Typical drugs that are affected by the multidrug resistance are doxorubicin, vincristine, vinblastine, colchicine and actinomycin D, and others. At least some multidrug resistance is a complex phenotype which has been linked to a high expression of a cell membrane drug efflux transporter called Mdr1 protein, also known as P-glycoprotein. This membrane "pump" has broad specificity and acts to remove from the cell a wide variety of chemically unrelated toxins. (See Endicott, J. A., et al. "The Biochemistry of P-Glycoprotein-Mediated Multidrug Resistance", Ann. Rev. Biochem. Vol. 58, pgs. 127–71, 1989.)

Recently, a similar mechanism of a broad spectrum drug resistance has been reported for certain microorganisms. These results indicate the existence of bacterial efflux systems of extremely broad substrate specificity that is similar to the multidrug resistance pump of mammalian cells. (See Nikaido, N., "Prevention of Drug Access to Bacterial Targets: Permeability Barriers and Active Efflux", Science, Vol. 264, pgs. 382–388, 1994; and Gottesman, M. M., et al. Annual Rev. Biochem., Vol 62, 385 1993)

Substances which reverse multidrug resistance are known as resistance modification agents (RMAs), and are of importance in potentiating the cytotoxicity of chemotherapeutic agents to which a human cancer has become resistant. Although many agents have been identified as RMAs in vitro, a large proportion have little or no therapeutic potential because of high toxicity in vivo at the doses required to reverse multidrug resistance. For example, metabolic poisons, such as azide, reverse multidrug resistance in vitro but have no usefulness in vivo. Most other highly effective RMAs, such as PSC833, appear to work as competitive antagonists of a drug binding site on the Mdr1 protein. Many of these agents also have toxicity which limits their usefulness in vivo. Consequently, there is a need to develop alternate pharmacological strategies for reversing multidrug resistance to provide RMAs with improved activity and lower overall toxicity.

Decreased intracellular drug accumulation through overexpression of the drug efflux Mdr1 protein is important to, but apparently not the only factor, in the multidrug resistance phenotype. Altered intracellular drug distribution and binding, among other possibilities, also seem to play a role. For example, the mechanism of reversing doxorubicin resistance using verapamil appears to be more related to altered intracellular distribution of doxorubicin than increased accumulation in the cell, as detailed in Schuurhuis, G. J., et al., "Quantitative determination of factors contributing to doxorubicin resistance in multidrug resistant cells," J. Natl. Cancer Inst., 81:1887–1892, 1989. In that report, it is shown that doxorubicin is concentrated almost exclusively in the nucleus in drug sensitive cells, and mainly in the cytoplasm in drug resistant cells. With the addition of verapamil, doxorubicin is localized mainly in the nucleus in drug resistant cells. Thus, high affinity binding of drugs to Mdr1 does not appear to be sufficient for optimal efflux, suggesting the existence of additional, rate limiting steps which may be susceptible to pharmacological intervention.

Certain non-ionic amphipathic surfactants, such as Tween 80 and CREMOPHOR® EL, have evidenced RMA activity. (See Riehm H., et al. "Potentiation of drug effect by Tween 80 in Chinese hamster cells resistant to actinomycin D and Danomycin" Cancer Res. Vol. 32, pgs. 1195–1200, 1972 and Woodcock, D. B., et al., "Reversal of the multidrug resistance phenotype with CREMOPHOR® EL, a common vehicle for water-insoluble vitamins and drugs" Cancer Res. Vol. 50, pgs. 4199–4203, 1990.) However, Tween 80 potentiates drug toxicity in both parental and multidrug resistant cells, calling into question the specificity of the Tween 80 effect on multidrug resistance. An effect on drug efflux has not been demonstrated. CREMOPHOR® EL is a complicated mixture of polyoxyethylated esters of triglycerides of mainly ricinoleic acid (castor oil), the composition and RMA active component of which have not been identified. Use of CREMOPHOR® EL in vivo is complicated by adverse histamine release in some patients. There have also been reports of neurotoxicity associated with the administration of CREMOPHOR® EL.

Cancer chemotherapy with cytotoxic agents can be successful only if the tumor cells are more sensitive than normal cells whose destruction is incompatible with survival of the host. Success, defined either as cure or clinically significant remission, is not readily explained by the still popular idea that tumor cells are more susceptible to cytotoxic agents because they are dividing more rapidly than vital normal cells, e.g. hematopoietic precursor cells. That rapid proliferation does not wholly account for the selective drug sensitivity of tumors is demonstrated by the common observations that some drug-sensitive cancers are not rapidly dividing, and that many rapidly proliferating tumors exhibit resistance. To say that the mechanisms accounting for the success or failure of chemotherapy for most human tumors is incompletely understood today is undoubtedly an understatement.

However, recent evidence suggests that the selectivity of chemotherapy for the relatively few tumors ever cured by drugs depends, to a large extent, upon their easy susceptibility to undergo apoptosis, i.e. to kill themselves. Many cytotoxic drugs that kill cells by crippling cellular metabolism at high concentration can trigger apoptosis in susceptible cells at much lower concentration. This appears to account for the unusual chemosensitivity of many lymphoid tumors, since many normal lymphocytes are "primed" to undergo self destruction as an essential part of the mechanism for generating and controlling diversity of the immune response. Increased susceptibility to apoptosis may also be acquired by tumor cells as a byproduct of the genetic changes responsible for malignant transformation. For example, tumor cells with constitutive c-myc expression may undergo apoptosis in response to DNA damage by anticancer agents, whereas normal cells are able to pause at checkpoints in the cell cycle to repair the damage, or may not be cycling at all, rendering them highly resistant to apoptosis in this setting.

Although some tumors are composed of cells which are highly sensitive to apoptotic stimuli, and others have a genetic changes which, in isolation, predispose to apoptosis, most tumors tend to acquire other genetic lesions which abrogate this increased sensitivity. Either at presentation or after therapeutic attempts, the tumor cells actually become less sensitive to apoptosis than vital normal dividing cells. Such tumors are generally not curable by available chemotherapeutic approaches. Decreased apoptotic response has been associated with increased malignant potential and has been shown to confer pleiotropic drug resistance by oncogene transfer techniques. Therefore, although previously recognized mechanisms of drug resistance, such as decreased drug uptake, altered intracellular drug localization, accelerated detoxification and alteration of drug target continue to be regarded as important factors, pleiotropic resistance due to defective apoptotic response has recently emerged as a distinct and significant category of drug resistance in cancer. Resistance due to failure to trigger apoptosis is sometimes called "downstream" drug resistance to distinguish it from the "classical" mechanisms mentioned above.

Thus, what is needed is a clearly identified class of compositions that reverse multidrug resistance in vivo. The composition should have a low occurrence of adverse side-effects. In addition, what is further needed is a composition and method for stimulating apoptosis in cancer cells.

SUMMARY OF THE INVENTION

The present invention comprises certain compositions that exhibit substantial RMA activity in cancers. One example of such a composition is a non-ionic amphipathic surfactant, known by the trade name SOLUTOL® HS 15 (BASF Corporation, Parsippany, N.J.). This composition increases the cytotoxicity of chemotherapeutic drugs in multidrug resistant cell lines, but not in drug sensitive cell lines, indicating that the potentiating effect is not due to the additive toxicity of the agent itself. The agent also promotes chemotherapeutic agent accumulation in multidrug resistant cells thereby potentiating the effect of the chemotherapeutic agent.

The present invention also comprises a method for reversing multidrug resistance in human or animal cancer cells and a composition for eliminating multidrug resistant human or animal cancer cells. One composition that is an aspect of the present invention is a particular fraction of SOLUTOL® HS 15 collected by reverse phase liquid chromatography or super critical extraction. It has been found that the RMA activity in the SOLUTOL® HS 15 resides in a narrow fraction from the reverse phase liquid chromatography. It has been further determined that the toxicity to cells which is inherent in SOLUTOL® resides in a fraction different from the fraction containing the RMA activity.

The present invention also includes a class of compounds that are ethoxylated fatty acids that exhibit strong RMA activity. These compounds have been found to be a polyethylene glycol with between approximately 4 to 100 ethylene oxide units with two fatty acids of between approximately 8 and 60 carbon atoms attached to the ends of the polymer in preferably an ester linkage. The fatty acid component of the present invention can be unsaturated or can have substitutions in the carbon chain. The ethoxylated compound is preferably of the present invention has the following general structure:

Fatty acid Polyethylene glycol Fatty acid

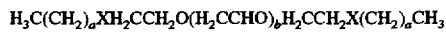

wherein the average of "a" is between approximately 8 and 30 and "b" is between 4 and 100 and X=CO—O (ester), CO—NH (amide) or O (ether). In a the preferred molecule, "a" is between 15 and 25 and "b" is between 12 and 40. In the most preferred molecule "a" is 16 and "b" is 18 and the molecule is a diester. This molecule is designated CRL 1095 and is available from CytRx Corporation, Atlanta, Ga.

The present invention also includes compositions and methods for reducing the resistance of certain microorganisms to chemotherapeutic agents. It has been determined that certain microorganisms contain P-glycoprotein-like pumping mechanisms that are similar to those found in mammalian cells and it is believed that these mechanisms may be important in resistance to antimicrobial agents. It has been reported that tetracycline is particularly susceptible to multidrug resistance in cells. Another embodiment of the present invention is the use of the compositions described herein to increase the effectiveness of tetracycline. According to the present invention, by administering tetracycline with the compositions described herein, the tissue concentration can be significantly increased. In addition, the duration of drug presence is also increased.

Anticancer drugs often kill tumor cells by inducing apoptosis, a form of cell death requiring active participation of the target cells. Impaired ability of cells to execute an apoptotic response results in pleiotropic drug resistance, and modulation of apoptosis resistance might improve the effectiveness of chemotherapy. Prominent involvement of the cell membrane in the pathways leading to apoptosis suggests the opportunity to modify the cellular sensitivity or threshold for apoptosis with membrane interactive agents. It is contemplated as part of the present invention compositions that are novel surfactants that reverse P-glycoprotein-mediated multidrug resistance with negligible toxicity of their own. Some of these agents can also potentiate cytotoxic drug-induced apoptosis, irrespective of P-glycoprotein expression. It is further an aspect of the present invention to provide compositions and methods for inhibiting the expression of genes that code for P-glycoprotein or other proteins that mediate the transport of chemotherapeutic agents. It is to be understood that the present invention includes the use of the disclosed compositions prophylactively in cancer therapy before the use of chemotherapy.

Another embodiment of the present invention are the polyoxyethylene/polyoxypropylene copolymers with the following general formula:

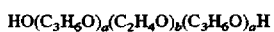

wherein the average of "a" is between approximately 20 and 60 and "b" is between approximately 10 and 30. A more preferable range is "a" of between approximately 30 and 50 and "b" of between approximately 15 and 25. It is to be understood that the propylene copolymer can be substituted with a butylene copolymer or even mixtures of butylene and propylene units.

The preferred copolymer is a polyoxyethylene/polyoxypropylene copolymers with the following general formula:

$$HO(C_3H_6O)_a(C_2H_4O)_b(C_3H_6O)_aH$$

wherein the average of "a" is approximately 40 and "b" is approximately 20 and is designated CRL 1605.

Accordingly, it is an object of the present invention to provide a composition and method for reducing or eliminating multidrug resistance in human or animal cancer cells.

It is further an object of the present invention to provide a composition and method for treating a human or animal with multidrug resistant cancer.

It is further an object of the present invention to provide a composition and method for reducing multidrug resistance which will not produce adverse side-effects.

It is another object of the present invention to provide a composition and method to block expression of the MDR1 gene or related genes.

It is further an object of the present invention to provide a composition and method that can be used to alter the blood brain barrier thereby allowing certain therapeutic agents to cross the barrier from the blood into the brain.

It is yet another object of the present invention to provide a composition and method for increasing the sensitivity of drug resistant microorganisms to chemotherapeutic agents.

It is yet another object of the present invention to provide a composition and method for increasing the efficacy and bioavailability of certain antimicrobial drugs such as tetracycline.

It is another object of the present invention to provide compositions and methods for altering the threshld for inducing apoptosis, especially in apoptosis-resistant cancers.

It is yet another object of the present invention to provide a composition and method that can be used to reverse multidrug resistance to VP-16 and VM-26 in cancer cells.

It is yet another object of the present invention to provide a composition and method for reducing the resistance of microorganisms to certain drugs.

These and other objects, features and advantages of the present invention will become apparent after a review of the following detailed description of the disclosed embodiment and the appended claims.

DETAILED DESCRIPTION

Figure 1:
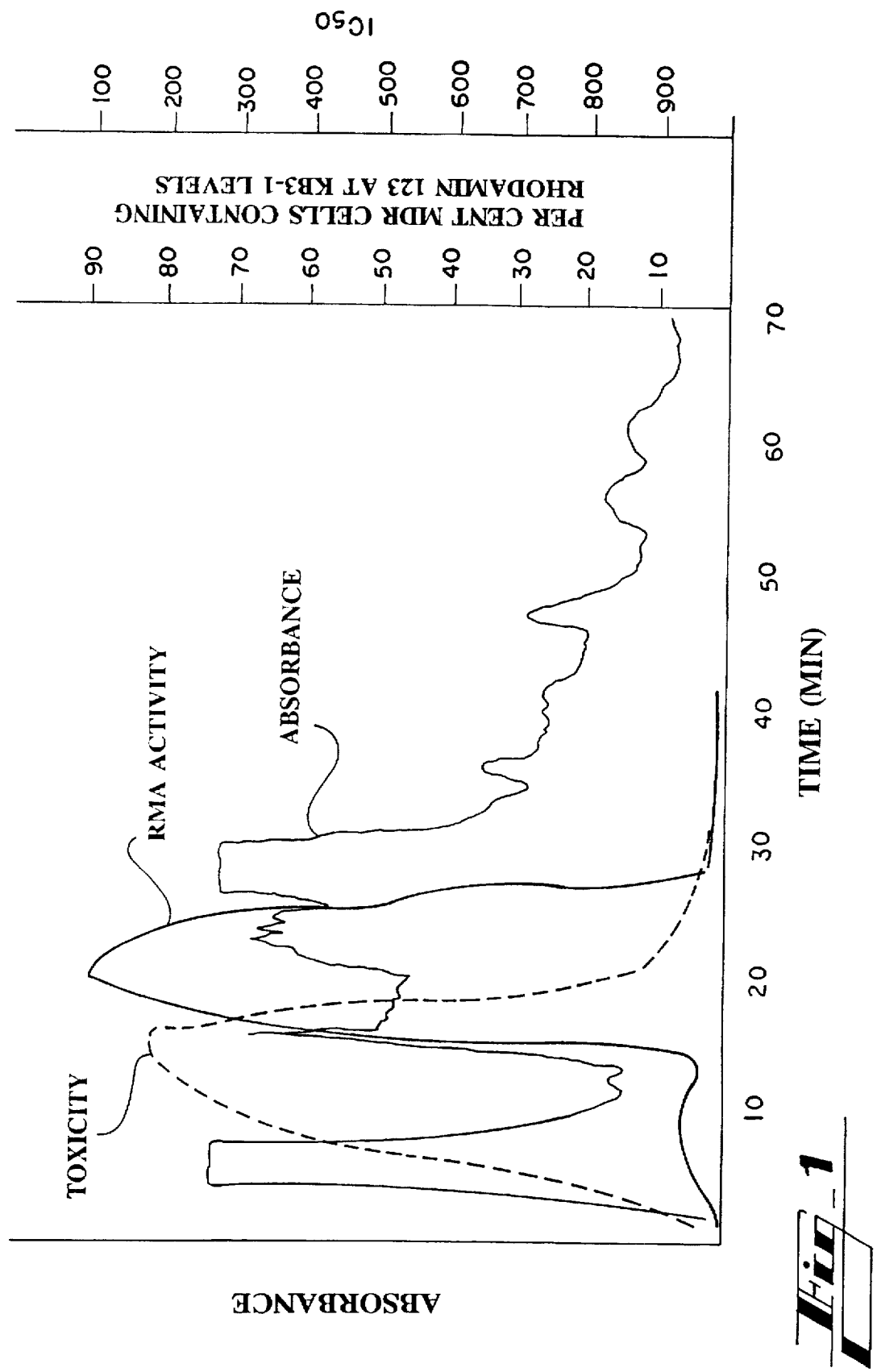
FIG. 1 shows fractionation of SOLUTOL® HS 15 using reverse phase liquid chromatography.

As used herein, the term "multidrug resistance" means resistance or acquired or natural resistance of tumor or microorganisms to chemotherapeutic agents. The multidrug resistance can be mediated by P-glycoprotein or can be mediated by other mechanisms. The term "patient" means either a human or animal with multidrug resistant cancer or a human or animal infected with a multidrug-resistant microorganism or a combination of microorganisms.

The present invention comprises methods and compositions for reducing or eliminating multidrug resistance in cancers in patients. According to the method and composition of the present invention, a non-ionic amphipathic ester or diester of a fatty acid is administered to a patient in which a cancer exhibits multidrug resistance to the chemotherapeutic agent. The method and composition of the present invention may be employed with particular efficacy where multidrug resistance to any chemotherapeutic agent has been conferred upon a cancer.

Another embodiment of the present invention is directed to compositions and methods for increasing the tissue concentration of certain antibiotics such as tetracycline. For example, tetracycline is believed to be excluded from tissues via the multidrug resistance pump. By administering the compositions described herein either with the tetracycline or shortly before or after administration of the tetracycline, the tissue concentration of the tetracycline can be increased.

The present invention includes a method of treating a patient with a cancer that exhibits multidrug resistance to reduce or eliminate the multidrug resistance which includes administering to the patient an effective amount of a non-ionic amphipathic diester of a fatty acid or a polyoxypropylene/polyoxyethylene copolymer. A preparation that exhibits the desired biologic activity is SOLUTOL® HS 15. This preparation is a mixture of various compounds with surfactant activities.

By fractionating the SOLUTOL® HS 15 preparation using reverse phase liquid chromatography and then assaying the various fractions for RMA activity, it has been determined that the RMA activity resides in a small fraction which contains fatty acid esters and diesters containing ethylene oxide units. This fraction has a much higher specific activity than the unfractionated SOLUTOL® HS 15.

In addition, fractionation of CREMOPHOR® EL by either reverse phase liquid chromatography or by super critical extraction shows that the RMA activity resides in a fraction which contains fatty acid esters and diesters containing ethylene oxide units.

By testing several fatty acid esters and diesters with varying ethylene oxide units, it has been found that compounds which are ethoxylated fatty acids exhibit strong RMA activity. These compounds have been found to be fatty acids or polymers of fatty acids with between approximately 8 and 60 carbon atoms and between approximately 4 to 100 ethylene oxide units. The fatty acid component of the present invention can be unsaturated and/or substituted and still exhibit activity. The preferred fatty acids are straight chained. In general, the fatty acids without the ethylene oxide units have little or no RMA activity.

It has been determined that the most active fraction of SOLUTOL® HS 15 and CREMOPHOR® EL are diesters of polyethylene glycol. For example, when native CREMOPHOR® EL was fractionated using supercritical extraction, as shown in Example VIII, 35 percent of the total preparation of CREMOPHOR® was extracted. The unextracted portion of the CREMOPHOR® showed little or no activity. Approximately 14% of the total CREMOPHOR® EL mixture was found to have significantly higher (10×) RMA activity compared to native CREMOPHOR® EL. The active fractions of CREMOPHOR® EL are less toxic than the native CREMOPHOR® EL. Infrared analysis of the active fraction shows that the fractions are polyethylene glycol/fatty acid diesters.

Thus, the present invention includes ethoxylated fatty acids. The fatty acids of the present invention have between 8 and 60 carbon atoms and between approximately 4 to 100 ethylene oxide units. The polyethylene glycol polymers have fatty acids attached, preferably via an ester linkage to both ends of the polyethylene glycol polymer. The fatty acids that are components of the RMA molecule of the present invention have between approximately 4 and 60 carbon atoms. The preferred compounds have a fatty acids with between 12 and 40 carbons with the more preferred compounds with between 8 and 30 carbon atoms with the most preferred compounds having between approximately 15 and 20 carbon atoms. It is to be understood that the two fatty acids in the diester can be different fatty acids. Preferred fatty acids include, but are not limited to, stearic acid, linoleic, oleic acid, palmitic acid and linolenic acid.

The preferred polyethylene glycol polymers in the RMA compounds have between approximately 4 and 100 ethylene oxide units, with the more preferred compounds having between 8 and 30 ethylene oxide units and the most preferred compounds having between 15 and 25 ethylene oxide units.

While not wanting to be bound by the following theory, it is believed that cellular membrane transport proteins must form polymers, usually dimers or tetramers, to effectively carry out their transport functions. Thus it is likely that the Mdr1 protein can achieve its function of removing from the cell a wide variety of chemically unrelated toxins only after forming polymers in the membrane. Non-ionic amphipathic surfactants exhibit membrane surface activity and are characterized by having a hydrophilic head and hydrophobic tail. In particular, non-ionic amphipathic esters of fatty acids, inhibit the formation of such protein polymers, and thereby inhibit drug efflux.

The ester of the present invention has a hydrophilic head, which comprises polyethylene glycol, and a hydrophobic tail comprising a fatty acid. Such a molecule is amphipathic. The molecule is large enough that each end displays its own solubility behavior. In another embodiment of the present invention, the polyethylene glycol has two hydrophobic fatty acid tails on either end of the polyethylene glycol polymer. The fatty acid tails are attached to the polyethylene glycol polymer preferably via an ester linkage, although the linkage can be via other bonds such as an ether linkage or an amide or similar linkage. The molecule has the following general structure:

Fatty acid Polyethylene glycol Fatty acid

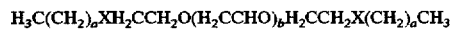

wherein the average of "a" is between approximately 8 and 30 and "b" is between 4 and 100 and X=CO—O (ester), CO—NH (amide) or O (ether). In a the preferred molecule, "a" is between 15 and 25 and "b" is between 12 and 40. In the most preferred molecule "a" is 16 and "b" is 18 and the molecule is a diester. This molecule is designated CRL 1095 and is available from CytRx Corporation, Atlanta, Ga.

Another embodiment of the present invention are compounds that are effective in reducing multidrug resistance in cancer cells that are polyoxyethylene/polyoxypropylene copolymers with the following general formula:

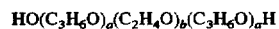

wherein the average of "a" is between approximately 20 through 60 and "b" is between approximately 5 and 50. It is to be understood that the propylene copolymer can be substituted with a butylene copolymer or even mixtures of butylene and propylene units.

The preferred copolymer is a polyoxyethylene/polyoxypropylene copolymer with the following general formula:

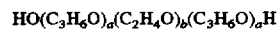

wherein the average of "a" is approximately 40 and "b" is approximately 20 and is designated CRL 1605.

The molecule may be administered to a patient either alone or in combination with a treatment program of at least one chemotherapeutic agent to which the human cancer is resistant. Such a chemotherapeutic agent typically includes, but is not limited to, doxorubicin, vincristine, vinblastine, Taxol, colchicine, VP-16 and actinomycin D. However, there are many other chemicals used in chemotherapy to which multidrug resistance may appear during treatment, and the present invention may be employed equally well in such cases. In addition, the present invention is useful for reducing resistance to platinum compounds by promoting accumulation of these compounds.

In general, at least one effective dose of the RMA of the present invention is administered for every dose of chemotherapeutic agent that is administered in treatment. Preferably, an effective dose of the RMA may be administered at least daily throughout the period between administration of successive doses of chemotherapeutic agent. The treatment period typically lasts about four weeks, depending upon the cancer being treated and the chemotherapeutic agents being used. Alternatively, the RMA may be continuously infused throughout said period. The administration of the RMA may also commence prior to a session of chemotherapy, and continue throughout and after the chemotherapy session. The amount of the RMA per dose will depend on which particular non-ionic amphipathic fatty acid ester is employed according to the present invention. However it is preferable that the maximum dosage that may be tolerated with negligible toxic symptoms in vivo be used. At least some non-ionic amphipathic esters of fatty acids, such as SOLUTOL® HS 15, are tolerated extremely well in vivo, and may be employed with no acute toxicity at dosages which achieve equivalent or superior reversal of multidrug resistance to common chemotherapeutic agents as compared to dosages of the prototypical RMA verapamil which produce marked toxicity.

The RMA of the present invention can be administered either intravenously or orally. It may be administered separately from the chemotherapeutic agent, as may be dictated by the chemotherapy, in which case the amount of time between commencing administration of the RMA and administration of the chemotherapeutic agent should not be substantial, e.g. typically within 24 hours, or as the chemotherapy permits. An exemplary treatment regimen comprises oral or intravenous administration of the RMA, followed by administration of the chemotherapeutic agent throughout the period until the next session of chemotherapy, either by continuous infusion or oral time release capsules. Although the optimal blood concentration of the RMA of the present invention will vary according to the chemotherapeutic agent being used or the type of cancer being treated, a typically preferred plasma concentration is between 0.1 to 5 mg/ml. A more preferred plasma concentration of RMA of the present invention is between approximately 0.5 mg/ml and 2.5 mg/ml. If a polyethylene glycol fatty acid diester or a reverse poloxamer which has been synthesized or purified is used to treat a patient with multidrug resistant cancer or microorganism infection, the preferred plasma concentration is between approximately 0.01 mg/ml and 2.5 mg/ml with the more preferred plasma concentration between approximately 0.1 mg/ml and 2 mg/ml.

Alternatively, the RMA of the present invention may be administered in combination with the chemotherapeutic agent, comprising continuous infusion or daily oral consumption of time release capsules of the RMA commencing prior to the chemotherapy session, and continuing throughout and after the session, by way of example. The RMA may be infused together through the same needle with the chemotherapeutic agent, or combined in a single oral capsule, as the chemotherapeutic agent permits, in which cases the RMA of the present invention may be used as an emulsifier of the agent, since non-ionic amphipathic esters of fatty acids commonly possess emulsifying characteristics. The RMA of the present invention preferably should be administered at least one hour prior to and during administration of a cancer chemotherapeutic agent. The RMA of the present invention should be given for at least 12 to 24 hours after administration of the cancer chemotherapy. However, the administration protocol will be dependent upon the pahrmacokinetics of the chemotherapy and RMA.

Preparation of an emulsion of the chemotherapeutic agent with the RMA will depend on the particular agents used. Typically, the RMA and the chemotherapeutic agent are combined and heated above room temperature to a range in which both the RMA and the chemotherapeutic agent are still stable, but in which the RMA becomes fluid, about 50° to 80° C. Sterile water is heated to the same temperature and then added with vigorous agitation in a proper amount to achieve a viscosity appropriate for administration. Other components may be added to the emulsion as necessary to prepare it either for intravenous or oral administration, as is well known in the art.

According to another embodiment of the present invention, the RMA of the present invention can be administered together with other RMAs, such as verapamil. The RMA of the present invention and a second RMA can be infused separately or concurrently, or combined into one time release capsule for oral consumption, in effective doses typically administered in treatment using each RMA alone, as permitted by the toxicity of the second RMA.

The formulations include those suitable for oral, rectal, nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the RMA or the present invention and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc. Desired parenteral formulation of the polyoxypropylene/polyoxyethylene block copolymers or the ethoxylated fatty acids may optionally contain solubilizers such as CHREMAPHORE or SOLUTOL.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation approximately isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

The method and composition of the present invention provide an important new means of overcoming multidrug resistance in human cancers. The method and composition have an efficacy equal to or better than best resistance modification agents known to the inventor. Furthermore the agent used in the method and composition of the present invention has a lower toxicity than other RMAs and fewer side effects than other potential RMAs. Moreover, it is believed that the agent operates by a different mechanism on the complex phenotype of multidrug resistance, and thus can be combined with other RMAs to provide a more potent means of reversing multidrug resistance.

The structure of SOLUTOL® HS 15 or other RMAs comprised of ethoxylated fatty acids is dissimilar to that of veraparnil or other typical RMAs. The markedly greater potency of SOLUTOL® HS 15 than verapamil for reversing VP-16 or colchicine resistance relative to the ability of each to reverse vinblastine or doxorubicin resistance supports the hypothesis that SOLUTOL® HS 15 operates by a MDR-reversing mechanism different from competition for the drug-binding site on Mdr1 protein found in verapamil. Colchicine is known to interact weakly with the identified drug-binding site on the Mdr1 protein, since colchicine does not compete for vinblastine binding. The fact that MDR cells are nevertheless highly resistant to colchicine indicates that colchicine efflux is less dependent on interaction with this drug-binding site than is vinblastine. Since SOLUTOL® HS 15 is a highly potent RMA for both colchicine and vinblastine, it may inhibit a second event necessary for efflux after drug binding, namely actual transport through the membrane. It is likely that SOLUTOL® HS 15, as a surfactant, inhibits formation of Mdr1 protein polymers which may be necessary to achieve drug efflux.

Another important advantage of the RMA of the present invention is the fact that the compounds which are contemplated as part of the present invention are highly effective against the multidrug resistance against the anticancer drug VP-16. The prior art RMAs, such as verapamil, are not effective against VP-16 multidrug resistance. (See Schested, M, et al. "Relationship of VP-16 to the Classical Multidrug Resistance Phenotype", *Cancer Research*, Vol. 52, pgs. 2874–2879, 1992.) The RMAs of the present invention have been found to be effective in reducing multidrug resistance against a broad spectrum of anticancer drugs.

It is well known that certain microorganisms contain membrane proteins which are similar in structure and function to the P-glycoprotein that is expressed by the Mdr1 gene in mammals. It is contemplated as part of the present invention that the methods and compositions that make up the present invention can be used to make certain microorganisms more susceptible to therapeutic drugs. For example, it is likely that the present invention will reverse chloroquine resistance in malaria.

Another embodiment of the present invention relates to the blood brain barrier. It has been reported that the P-glycoprotein pump exists in brain capillary endothelium. (See Tasuta, T., et al., "Functional Involvement of P-glycoprotein in Blood-Brain Barrier", *J. Biol. Chem.*, Vol. 267, pgs. 20383–20391, 1992.) The brain is a pharmacological sanctuary in that many drugs administered systemically have limited access to the tissue parenchyma. In the brain, endothelial cells forming the capillary tube are joined by continuous tight junctions that prevent many substances from entering the organ. Nutrients needed for brain cells are selectively transported from the blood through specific channels or transporters in the capillary endothelial cells. Thus, the brain is a rigorously isolated compartment that is protected by a blood-brain barrier. Hydrophobic antitumor agents, such as Vinca alkaloid and adriamycin (ADM), cannot enter the brain, although other hydrophobic molecules such as nicotine and ethanol readily pass through the blood-brain barrier. Therefore, some mechanisms of the barrier that selectively block the penetration of lipid-soluble antitumor agents into the brain could exist. The presence of P-glycoprotein in the capillary endothelium has been reported in both brain and testis but not in the other tissues. This suggests the functional involvement of P-glycoprotein in the blood-brain barrier. It is contemplated as part of the present invention that the methods and compounds described herein can be used to reduce the blood-brain barrier thereby allowing beneficial therapeutic agents to cross the barrier.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

Cell lines and culture conditions

The drug sensitive human carcinoma cell line, KB 3-1, and the MDR variants, KB 8-5-11 and KB V-1 used in this study were generously provided by Dr. M. Gottesman, NCI, Bethesda, Md. The properties of these cells and their culture conditions have been previously described in detail (Akiyama, et al., Isolation and genetic characterization of human KB cell lines resistant to multiple drugs. *Somat. Cell. Molec. Genet.*, 11, 117–126 (1985)). The KB 8-5-11 cell line was maintained medium containing 100 ng/ml colchicine (Sigma, St. Louis, Mo.) and the KB V-1 cell line was maintained in medium containing 1 mg/ml vinblastine (donated by Eli Lilly and Co., Indianapolis, Ind.).

Human epidermoid carcinoma cell lines KB 8-5 and KB 8-5-11, which exhibit multidrug resistance, and their parental cell line KB 3-1, which is drug sensitive, were treated in vitro with SOLUTOL® HS 15 in combination with various chemotherapeutic agents, namely colchicine, vinblastine, and doxorubicin. The details of the treatment are described in Coon, J. S., et al, "SOLUTOL® HS 15, nontoxic polyoxyethylene esters of 12-hydroxystearic acid, reverses multidrug resistance", *Cancer Research*, 51, 897–902, 1991, which is incorporated by reference. Cell Lines and Culture Conditions. The MDR cell lines KB 8-5 and KB 8-5-11 and the parental, drug-sensitive KB 3-1 were generally provided by Dr. Michael Gottesman's laboratory. The characteristics of these human epidermoid carcinoma cell lines have been described in detail elsewhere (Akiyama, S., et al., "Isolation and genetic characterization of human KB cell lines resistant to multiple drugs," *Somat. Cell. Mol. Genet.*, 11:117–126, 1985). Cells were grown as adherent monolayers on 80 cm$^2$ flasks (Nunc, Roskilde, Denmark) in DMEM (pH 7.4) with 2 mM L-glutamine, nonessential amino acids, and vitamins (Gibco, Grand Island, N.Y.) with 10% fetal bovine serum (Hyclone, Logan, Utah), penicillin (50 units/ml), and streptomycin (50 µg/ml) (Sigma). To prevent loss of the MDR phenotype, KB 8-5 cells were maintained in 25 nM colchicine and KB 8-5-11 in 250 nM colchicine. All cell cultures were split at 1:5 twice weekly for routine maintenance. After 10 to 12 passages, new aliquots of frozen cells were thawed for further experiments. The presents of Mycoplasma was excluded by the Gen-Probe Rapid Detection System-Mycoplasma TCII (Gen-Probe, San Diego, Calif.).

Determination of $IC_{50}$. To assess the effect of different concentrations of Solutol HS 15 and verapamil (Abbott Laboratories, North Chicago, Ill.) on the $IC_{50}$ of colchicine (Sigma), vinblastine (Sigma), and doxorubicin (Farmitalia Carlo Erba, Milan, Italy), two dimensional titrations in 96 wells (16 mm) in plastic plates (Falcon; Becton-Dickinson, Lincoln Park, N.J.) were performed with increasing concentrations of cytotoxic drug along one axis and increasing concentrations of a RMA along the other. One-dimensional tirations were performed to determine the $IC_{50}$ of individual drugs. Two×10$^4$ cells were plated in each well and incubated without drug for 24 h to permit attachment and resumption of growth. The desired concentrations of drugs were then added, and the cells were incubated for an additional 5 days. Wells were washed with phosphate-buffered saline and adherent cells were stained with crystal violet (Sigma) (Kuenig, W. et al., "Quantification of cells cultured on 96-well plates," *Anal. Biochem.*, 182:16–19, 1989). Cell-associated dye was then solubilized with 10% acetic acid and the viable (adherent) cell number was assessed by measuring the concentration of stain in the wells with a Dynatech model MR 700 spectrophotomer (Chantilly, Va.) at 570 nm (Kuenig, W. et al., "Quantification of cells cultured on 96-well plates," *Anal. Biochem.*, 182:16–19, 1989). The accuracy of this method was verified by counting trypsinized cells in a hemacytometer in a duplicate experiment (data not shown). Briefly, cells from the three lines were plated as is well known in the art in 96-well plates, with increasing concentrations of cytotoxic drug along one axis of the plate and increasing concentrations of the RMA along the other axis of the plate. After incubation for five days, the plates were washed and dyed according to methods known in the art, and a cell count was determined. The mean concentration of the cytotoxic drug that caused 50% inhibition of cell growth compared to controls ($IC_{50}$) was plotted at various concentrations of the RMA. Complete reversal of the MDR phenotype in KB 8-5 and KB 8-5-11 cells was achieved by SOLUTOL® HS 15, while the RMA did not potentiate drug toxicity in drug-sensitive KB 3-1 cells, indicating the potentiating effect was not due to any toxicity of SOLUTOL® HS 15 itself. At a concentration of 10% of its own $IC_{50}$, SOLUTOL® HS 15 produced a marked reduction in the resistance of KB 8-5-11 cells to colchicine, vinblastine, and doxorubicin.

Identical platings were also performed for the prototypical RMA verapamil. Unexpectedly, the relation between the effects that SOLUTOL® HS 15 had on the three cytotoxins was different from the relation between the effects that verapamil had on the three cytotoxins, indicating SOLUTOL® HS 15 and verapamil affect multidrug resistance by different mechanisms. SOLUTOL® HS 15 was relatively much more potent than verapamil for reversing colchicine resistance, as compared to the ability of each RMA to reverse vinblastine resistance.

EXAMPLE II

Human epidermoid carcinoma cell lines KB 8-5 and KB 8-5-11, which exhibit multidrug resistance, and their parental cell line KB 3-1, which is drug sensitive, were treated in vitro with SOLUTOL® HS 15 in combination with various chemotherapeutic agents, namely colchicine, vinblastine, and doxorubicin. The details of the treatment are described in Coon, J. S., et al, "SOLUTOL® HS 15, nontoxic polyoxyethylene esters of 12-hydroxystearic acid, reverses multidrug resistance", *Cancer Research*, 51, 897–902, 1991, which is incorporated by reference.

Cell Lines and Culture Conditions. The MDR cell lines KB 8-5 and KB 8-5-11 and the parental, drug-sensitive KB 3-1 were generously provided by Dr. Michael Gottesman's laboratory. The characteristics of these human epidermoid carcinoma cell lines have been described in detail elsewhere (Akiyama, S., et al., "Isolation and genetic characterization of human KB cell lines resistant to multiple drugs," *Somat. Cell. Mol. Genet.*, 11:117–126, 1985). Cells were grown as adherent monolayers on 80 cm$^2$ flasks (Nunc, Roskilde, Denmark) in DMEM (pH 7.4) with 2 mM L-glutamine, nonessential amino acids, and vitamins (Gibco, Grand Island, N.Y.) with 10% fetal bovine serum (Hyclone, Logan, Utah), penicillin (50 units/ml), and streptomycin (50 µg/ml) (Sigma). To prevent loss of the MDR phenotype, KB 8-5 cells were maintained in 25 nM colchicine and KB 8-5-11 in 250 nM colchicine. All cell cultures were split at 1:5 twice weekly for routine maintenance. After 10 to 12 passages, new aliquots of frozen cells were thawed for further experiments. The presents of Mycoplasma was excluded by the Gen-Probe Rapid Detection System-Mycoplasma TCII (Gen-Probe, San Diego, Calif.).

Determination of $IC_{50}$. To assess the effect of different concentrations of Solutol HS 15 and verapamil (Abbott Laboratories, North Chicago, Ill.) on the $IC_{50}$ of colchicine (Sigma), vinblastine (Sigma), and doxorubicin (Farmitalia Carlo Erba, Milan, Italy), two dimensional titrations in 96 wells (16 mm) in plastic plates (Falcon; Becton-Dickinson, Lincoln Park, N.J.) were performed with increasing concentrations of cytotoxic drug along one axis and increasing concentrations of a RMA along the other. One-dimensional tirations were performed to determine the $IC_{50}$ of individual drugs. Two×10$^4$ cells were plated in each well and incubated without drug for 24 h to permit attachment and resumption of growth. The desired concentrations of drugs were then added, and the cells were incubated for an additional 5 days. Wells were washed with phosphate-buffered saline and adherent cells were stained with crystal violet (Sigma) (Kuenig, W. et al., "Quantification of cells cultured on 96-well plates," *Anal. Biochem.*, 182:16–19, 1989). Cell-associated dye was then solubilized with 10% acetic acid and the viable (adherent) cell number was assessed by measuring the concentration of stain in the wells with a Dynatech model MR 700 spectrophotomer (Chantilly, Va.) at 570 nm (Kuenig, W. et al., "Quantification of cells cultured on 96-well plates," *Anal. Biochem.*, 182:16–19, 1989). The accuracy of this method was verified by counting trypsinized cells in a hemacytometer in a duplicate experiment (data not shown). Briefly, cells from the three lines were plated as is well known in the art in 96-well plates, with increasing concentrations of cytotoxic drug along one axis of the plate and increasing concentrations of the RMA along the other axis of the plate. After incubation for five days, the plates were washed and dyed according to methods known in the art, and a cell count was determined. The mean concentration of the cytotoxic drug that caused 50% inhibition of cell growth compared to controls ($IC_{50}$) was plotted at various concentrations of the RMA. Complete reversal of the MDR phenotype in KB 8-5 and KB 8-5-11 cells was achieved by SOLUTOL® HS 15, while the RMA did not potentiate drug toxicity in drug-sensitive KB 3-1 cells, indicating the potentiating effect was not due to any toxicity of SOLUTOL® HS 15 itself. At a concentration of 10% of its own $IC_{50}$, SOLUTOL® HS 15 produced a marked reduction in the resistance of KB 8-5-11 cells to colchicine, vinblastine, and doxorubicin.

Identical platings were also performed for the prototypical RMA verapamil. Unexpectedly, the relation between the effects that SOLUTOL® HS 15 had on the three cytotoxins was different from the relation between the effects that verapamil had on the three cytotoxins, indicating SOLUTOL® HS 15 and verapamil affect multidrug resistance by different mechanisms. SOLUTOL® HS 15 was relatively much more potent than verapamil for reversing colchicine resistance, as compared to the ability of each RMA to reverse vinblastine resistance.

EXAMPLE III
Measurement of cellular rhodamine 123 accumulation by flow cytometry Efflux of rhodamine 123 from MDR cells was also examined to provide direct information about the action of the transport protein Mdr 1. Enhanced accumulation of the P-gp substrate, rhodamine 123, in multidrug resistant KB 8-5-11 cells was used to measure RMA activity. Flow cytometric analysis was performed as described (Coon et al., 1991; Buckingham et al. 1995). Briefly, multidrug resistant KB 8-5-11 cells ($0.5 \times 10^6$ cells/ml) were incubated with 0.5 mg/ml rhodamine 123 at 37° C. in the presence or absence of the putative RMA. After 60 min., mean intracellular steady state rhodamine 123 fluorescence was measured on an Epics Profile Flow Cytometer (Coulter, Hialeah, Fla.). Increased rhodamine 123 accumulation in MDR cells has been shown to correlate quantitatively with inhibition of MDR activity (Kessel, 1989; Efferth et al., 1989; Neyfakh, 1988).

EXAMPLE IV
Cell proliferation inhibition assay $IC_{50}$ (the drug concentration that reduces cell proliferation to 50% of untreated controls) was assessed as previously described (18). The chromogenic substrate, MTT (Sigma), was used to enumerate viable cells. Cyclosporine A was a gift from Sandoz (Basel, Switzerland) and verapamil Hcl was from Knoll (Whippany, N.J.). For the Resistance Modification Index (RMI, Eliason et al., 1990), cells were prepared in microtiter plates and incubated with the indicated drugs and RMA. RMI was calculated as the $IC_{50}$ of drug alone/$IC_{50}$ of drug+RMA. The average RMI was calculated from at least three independent assays.

EXAMPLE V

SOLUTOL® HS 15 was fractionated using reverse phase liquid chromatography to determine where the activity resides in the preparation. An approximately 50% solution of SOLUTOL® HS 15 was prepared in 100% acetonitrile (ACN) and water. One ml of the SOLUTOL® HS 15 solution was injected onto a Phenomenex IB-Sil reversed phase column. The column has 5 µm particles, and is 4.6 mm internal diameter by 150 mm. The flow rate was 2.0 ml/min. The mobile phase was as follows: A=5% ACN and B=100% ACN. The gradient was linear with 100% A to 100% B in 15 minutes, then was maintained at 100% B. Fractions were collected at 30 second intervals. The various fractions were assayed for RMA activity as described in Example III. The results of the fractionation are shown in FIG. 1. In addition the same fractions were assayed for toxicity by measuring 50% inhibitory concentrations ($IC_{50}$) as described in Kessel D., "Exploring Multidrug Resistance using Rhodamine 123", *Cancer Communications* Vol 1, pgs. 145–149, 1989.

As can be seen in FIG. 1, the RMA activity is confined in a single peak which elutes at approximately 20 minutes into the chromatographic run. The toxicity is confined to another peak that elutes before the activity peak and slightly overlaps the RMA peak. However, it is clear that most of the material that is responsible for the RMA activity is non-toxic.

EXAMPLE VI
Synthesis of fatty acid PEG-fatty acid diesters

Fatty acid diesters were synthesized by transesterification of PEG and fatty acid methyl esters (Malkemus, 1956). Stearic acid diester (CRL 1095) was synthesized from 2 moles of methyl stearate (Sigma) and 1 mole of PEG 900 in a reaction catalyzed by zinc acetate. The reaction temperature was kept at 160° C. for 5 hrs. under high vacuum (5 microns) with slight stirring. After 8 hrs. of reaction, the product was heated with magnesium silicate adsorbent at 120° C. for 6 hrs. and filtered. The product was washed twice with deionized water to remove the residual zinc acetate, discarding the aqueous phase. The final diester product was analyzed as 99% diester by HPLC. Other diesters were synthesized in a similar manner by substituting appropriate PEG and fatty acid starting materials. The resulting diesters were hydrophobic and were therefore dissolved in 95% alcohol to make stock solutions.

Synthesis of distearyl ether

Distearyl ether was synthesized by reacting stearyl bromide (Sigma) with PEG-900 in the presence of potassium hydroxide. Stearyl bromide (4.168 g in 10 ml toluene) was slowly added with stirring to 4.64 g of PEG-900 in 10 ml of toluene at 45° C. The mixture was then stirred at 60° C. for 30 min. and refluxed for 6 hrs. The final product was treated with charcoal, filtered and isolated from toluene.

Synthesis of distearyl amide

Distearyl amide was synthesized by reacting amine-modified PEG (Huntsman, Austin Tex.) with fatty acid chloride (Sigma). Stearyl chloride (0.61 g; Aldrich) was slowly added with stirring to 0.9 g of amine-modified PEG-900 and 2 moles of potassium hydroxide in a carbon tetrachloride/water mixture at room temperature. The carbon tetrachloride layer was separated and evaporated to produce the white powder of the diamide product (yield 68%).

Synthesis of fatty acid-PEG monoesters

To optimize the yield of monoesters in the ethoxylation reaction, a procedure different from that for making ethoxylated oleic acid (Example VII) was used. Approximately 1 mole of stearic, oleic or capric acid (Sigma) was mixed with 1 mole of PEG 600, PEG 900 or PEG 1500 (Aldrich, Milwaukee, Wis.) at a ratio of 1:1.1 fatty acid:PEG. The reactions were carried out as described (Wrigley et al., Synthetic detergents from animal fats. Ethenoxylation of fatty acids and alcohols. *J. Amer. Oil Chem. Soc.* 34, 39–43 (1957); for 8–12 hrs. in the presence of 1% para-toluenesulfonic acid catalyst (Sigma). After removal of the water byproduct and the toluene, the final product was dissolved in dichloromethane and washed with water. The dichloromethane solvent was then evaporated. The reaction products were analyzed by HPLC and found to be approximately 67 to 73% monoester, the remaining material being diester, PEG and traces of free fatty acid.

This presumably reflects the requirement for proper hydrophile-lipophile balance (HLB) of the active molecule. A series of PEG domains of average MW 600, 900 or 1500 was synthesized. The results from rhodamine123 analyses of these compounds is shown in Table II. The optimal average MW of the PEG domain in diesters was also found to be 900, corresponding to about 20 ethylene oxide units (ethylene oxide ~44 MW).

TABLE II

COMPARISON OF RHODAMINE123 ACCUMULATION IN MDR KB8-5-11 CELLS TREATED WITH DIESTERS: EFFECT OF DEGREE OF ETHOXYLATION AND FATTY ACID

| Fatty Acid | PEG MW | mg/ml | MFI[1] |
|---|---|---|---|
| (No treatment) | | | 1 |
| Capric (C10:0) | 600 | 1 | 12 |
| | | 10 | 14 |
| | 900 | 1 | 11 |
| | | 10 | 12 |
| | 1500 | 1 | 10 |
| | | 10 | 11 |
| Stearic (C18:0) | 600 | 1 | 11 |
| | | 10 | 11 |
| | 900 | 1 | 29 |
| | | 10 | 87 |
| | 1500 | 1 | 12 |
| | | 10 | 30 |
| Oleic (C18:1) | 600 | 1 | 20 |
| | | 10 | 44 |
| | 900 | 1 | 21 |
| | | 10 | 70 |
| | 1500 | 1 | 12 |
| | | 10 | 24 |
| Linolenic (C18:3) | 600 | 1 | 17 |
| | | 10 | 40 |
| | 900 | 1 | 11 |
| | | 10 | 17 |
| | 1500 | 1 | 11 |
| | | 10 | 14 |

KB8-5-11 cells were exposed to each agent for 60 min. at 37° C. in the presence of 0.5 mg/ml rhodamine123. Accumulation of rhodamine123 was determined as described in Materials and Methods.
[1]Mean fluorescence intensity resulting from intracellular rhodamine123; average of three experiments.

EXAMPLE VII
Synthesis of Ethoxylated oleic acid

Ethoxylated oleic acid was synthesized as described using established methods (Wrigley et al., Synthetic detergents from animal fats. Ethenoxylation of fatty acids and alcohols. *J. Amer. Oil Chem. Soc.* 34, 39–43 (1957); Malkemus, Production of alkylene oxide derivatives. *J. Amer. Oil Chem. Soc* 33, 571–574 (1956)). Ethoxylated oleic acid was synthesized by reacting ethylene oxide with high purity oleic acid. About 1.38 grams of oleic acid (Sigman Chemical Co., St. Louis, Mo.) was allowed to react with 4.45 grams of ethylene oxide (Proxair, Inc. Knoxville, Tenn.) in the presence of cesium hydroxide catalyst (Cabot Performance Materials, Revere, Pa.) at about 100° C. The final product is heated with magnesium silicate adsorbent at 120° C. for six hours, cooled, and eluted with tetrahydrofuran. The product was isolated by evaporating the tetrahydrofuran solution.

Ethoxylated oleic acid was fractionated by gradient reverse phase liquid chromatography on a Waters LC Module I with gradient controller (Model 600), auto-sampler (Model 717), a UV detector (Model 486), and Millenium Software (Waters, Milford, Mass.). The sample solution was 2% ethoxylated oleic acid produced above in dichloroethane. The sample was applied to a Lichrosorb 5μ Diol, 250 mm×4.0 mm column. The injection volume was 200 μl with a flow rate of 2.5 mL/min. The mobile phases were A: 100% dichloroethane and B: 100% reagent alcohol. The gradient was as follows:

| | % A | % B | Curve |
|---|---|---|---|
| Initial | 100 | 0 | |
| 1.0 min | 100 | 0 | 6 (Linear) |
| 5.0 min | 95 | 5 | 6 (Linear) |
| 8.0 min | 100 | 0 | 11 (Ramp at 8.0 min) |

Gradient descriptions

From 0 to 1 minute, mobile phase is 100% A and 0% B.

From 1.0 minute to 5.0 minute, mobile phase changes linearly from 100% A and 0% B to 95% A and 5% B.

From 5.0 minute to 8.0 minute, mobile phase concentration remains at 95% A and 5% B.

At 8.0 minute, mobile phase changes to 100% A and 0% B (ramp).

The total run time was 12 minutes and fractions were collected every 30 seconds.

The various fractions obtained from the reverse phase liquid chromatography were analyzed to determine the RMA activity in each fraction. The fractions were then analyzed by infrared spectrophotometry.

Briefly, in the IR spectrum of unfractionated Ethoxylated oleic acid, bands around 2800 $cm^{-1}$–3000 $cm^{-1}$ can be assigned to aliphatic C—H stretching, whereas, band around 1740 $cm^{-1}$ and 1100 $cm^{-1}$ can be assigned to carbonyl stretching (C=O) and ether stretching (C—O—C) respectively. Relative intensity of these bands can be used to distinguish between a monoester and diester type species. For example, diesters have a higher amount of C—H and C=O linkages as compared to C—O—C linkages on a molar basis. Thus for diesters, one would expect to observe relatively higher intensities for aliphatic stretching (C—H, 2800 $cm^{-1}$–3000 $cm^{-1}$) and carbonyl stretching (C=O, 1740 $cm^{-1}$) when compared to intensity for ether stretching (C—O—C, 1100 $cm^{-1}$). Analysis of IR spectra of active fractions of Ethoxylated oleic acid suggests relatively higher (or equal) intensities for aliphatic stretching (C—H, 2800 $cm^{-1}$–3000 $cm^{-1}$) and carbonyl stretching (C=O, 1740 $cm^{-1}$) as compared to intensity for ether stretching (C—O—C, 1100 $cm^{-1}$).

Each sample was analyzed on a Magna IR Spectrometer, Model 550 When an IR spectral library search was conducted for above fractions, best match was obtained with the spectrum from the IR spectral libraries. Based on IR results and the subsequent IR library search, the active fractions of Ethoxylated oleic acid are predominately diester-type species.

The results of the analysis of the fractions are shown in Table III.

TABLE III

| Fraction # | % DCE | % EtOH | Amount mg | Relative RMA Activity | Mp/# of peaks |
|---|---|---|---|---|---|
| Control | — | — | — | 0.9 | — |
| 1 | 100 | 0 | >0.5 | 24.7 | — |
| 2 | 100 | 0 | >0.5 | 0.9 | — |
| 3 | 99.69 | 0.313 | >0.5 | 0.7 | 854/2 |
| 4 | 99.06 | 0.934 | >0.5 | 10.3 | 1151/3 |
| 5 | 98.44 | 1.563 | >0.5 | 95.3 | 1363/3 |
| 6 | 97.81 | 2.188 | 0.8 | 55.7 | 1488/3 |
| 7 | 97.19 | 2.813 | 0.8 | 88.9 | 1586,360/3 |
| 8 | 96.56 | 3.438 | 0.7 | 73.6 | 1627/4 |
| 9 | 95.94 | 4.063 | 0.5 | 84.3 | 1671/1 |
| 10 | 95.31 | 4.688 | 0.5 | 89.4 | 1693/1 |
| 11 | 95 | 5 | 1 | 92.5 | 1834/3 |
| 12 | 95 | 5 | 5.3 | 87.2 | 1346/B[b] |
| 13 | 95 | 5 | 4.8 | 26.8 | 1810/B |
| 14 | 95 | 5 | 1.5 | 2.2 | 978/1 |
| 15 | 95 | 5 | 3.8 | 1.8 | 1314/2 |
| 16 | 95 | 5 | >0.5 | 1.3 | 1432/2 |
| 17 | 95–100 | 5.0–0 | >0.5 | 1 | 1098/B |
| 18 | 100 | 0 | >0.5 | 1.4 | 1282/1 |
| 19 | 100 | 0 | >0.5 | 0.8 | 1098/B |
| 20 | 100 | 0 | >0.5 | 1 | 357/1 |
| Col. Wash | — | — | — | — | 864/1 |
| PEG-Oleic Acid | — | — | — | 62.3 | 1380/2 |
| Oleic Acid | — | — | — | — | 355/1 |

[a]Per cent cells KB8-5-11 (MDR) showing rhodamine 123 fluorescence in the range of sensitive cell (KB3-1) in the same experiment.
[b]Broad peak Infrared analysis of each fraction indicated that the active fractions contained at least one polyethylene glycol diester.

EXAMPLE VIII

CREMOPHOR® EL was fractionated by super critical extraction. Approximately 25 grams of CREMOPHOR® EL was thoroughly mixed with 20 grams of hydromatrix (silicon dioxide) manufactured by Varian-Harbor City, Calif. 40710 and loaded into a stainless steel high pressure extraction cell. The extraction cell was maintained at 40° C. Supercritical carbon dioxide was pumped into the extraction cell at a rate of approximately 3 liters of gaseous carbon dioxide per minute (4 ml of supercritical carbon dioxide per minute). The extractable material was dissolved under the extraction conditions, and separated from the matrix. The supercritical carbon dioxide solution with dissolved component was then depressurized to evaporate the carbon dioxide gas, and to precipitate the solute. Extraction was done at various pressures of carbon dioxide and fractions were collected at each pressure from 2000 psi to 7000 psi with 400 psi intervals.

Under these experimental conditions, 35 percent of the total CREMOPHOR® preparation was extracted. About 14 percent of the total CREMOPHOR® EL preparation was found to have significantly higher RMA activity than the native CREMOPHOR® EL. The portion of the CREMOPHOR® that was not extracted had minimal RMA activity. The results of the RMA activity measurements on the super critical fractions of CREMOPHOR® EL are shown in the following Table IV.

TABLE IV

| Agent | Relative RMA Activity[a] |
|---|---|
| None | 0.5 |
| SOLUTOL ® (100µg/ml) | 73 |
| CREMOPHOR ® EL (10 µg/ml) | 3.9 |
| CREMOPHOR ® EL (100µg/ml) | 29 |
| CREMOPHOR ® Fractions | |
| 45B 10 µg | 1.5 |
| 45B 100 µg | 4.1 |
| 46A 10 µg | 7.5 |
| 46A 100 µg | 56 |
| 46B 10 µg | 10 |
| 46B 100 µg | 73 |
| 46C 10 µg | 19 |
| 46C 100 µg | 94 |
| 46D 10 µg | 26 |
| 46D 100 µg | 97 |
| 47A 10 µg | 30 |
| 47A 100 µg | 99 |
| 47B 10 µg | 30 |
| 47B 100 µg | 98 |
| 47C 10 µg | 20 |
| 47C 100 µg | 97 |
| 47D 10 µg | 24 |
| 47D 100 µg | 92 |
| 48A 10 µg | 9.8 |
| 48A 100 µg | 82 |
| 49A 10 µg | 11 |
| 49A 100 µg | 74 |
| 49B 10 µg | 6.7 |
| 49B 100 µg | 66 |

[a]Per cent KB8-5-11 (MDR) cells showing rhodamine 123 fluorescence in the range of sensitive cell (KB3-1) in the same experiment.

The active fractions were found to be about half as toxic than native CREMOPHOR® as shown by $IC_{50}$ measurements.

EXAMPLE IX

The RMA activity of various fatty acids, PEG monoesters and PEG diesters was determined by the method described in Example III. The results of these experiments are shown in Table V.

TABLE V

| | | | (T/U)[b] | |
|---|---|---|---|---|
| | | Relative RMA | MFI | |
| Agent | µg/ml[a] | Activity[a] | KB3-1 | KB8-5-11 |
| None | | 0.6 | 1.0 | 1.0 |
| None + 10 µl EtOH | | 0.5 | 1.2 | 0.9 |
| Stearic Acid | 100 | 2.1 | 1.9 | 1.4 |
| Oleic Acid | 100 | 2.7 | 2.1 | 1.7 |
| Linolenic Acid | 10 | 1.3 | 1.2 | 0.9 |
| | 100 | 9.2 | 1.7 | 1.7 |
| PEG-600-monostearate | 10 | 0.4 | 1.3 | 1.1 |
| | 100 | 0.6 | 1.1 | 1.2 |
| PEG-600-distearate | 10 | 8.6 | 1.1 | 2.5 |
| | 100 | 31 | 0.9 | 5.5 |
| PEG-400-distearate | 10 | 5.0 | 1.0 | 1.8 |
| | 100 | 13 | 0.8 | 3.6 |
| PEG-900-monolinolenic | 10 | 45 | 0.6 | 3.6 |
| | 100 | 96 | 0.5 | 8.9 |
| PEG-900 dilinolenic | 10 | 98 | 0.5 | 11 |
| | 100 | 99 | 0.6 | 14 |
| PEG-900 dicapric | 10 | 8.7 | 0.8 | 1.3 |
| | 100 | 21 | 0.8 | 2.0 |

TABLE V-continued

| | (T/U)[b] | | |
|---|---|---|---|
| | | Relative RMA | MFI |
| Agent | μg/ml[a] | Activity[a] | KB3-1 | KB8-5-11 |
|---|---|---|---|---|
| PEG-900 distearate | 10 | 96 | 0.7 | 9.8 |
| | 100 | 97 | 0.6 | 9.9 |

[a]Per cent KB8-5-11 (MDR) cells showing rhodamine 123 fluorescence in the range of KB3-1 (sensitive) cells in the same experiment.
[b]Mean Fluorescence Intensity resulting from intracellular rhodamine 123 expressed as mean fluorescence of treated cells/mean fluorescence of untreated cells (168 for KB3-1 and 6.5 for KB8-5-11).

As shown in Table V, PEG 600 stearic acid diester is more active (31%) than PEG 400 stearic acid diester (13%). The PEG 900 diesters containing two linolenic acids or two stearates had greater activity then the corresponding PEG 900 monoesters. The free fatty acids and the monoesters only show minimal RMA activity. It should also be noted that the PEG 900 dicapric acid (8 carbons) showed minimal activity. The ratio of hydrophil (EO) to hydrophobe (fatty acid) in the G 900 dicapric acid is not optimal.

EXAMPLE X

Examples X through XX are directed to CRL-1095. This molecule has the following structure:

wherein the average of "a" is 16 and "b" is 18 and X is an ester linkage. This molecule is available from CytRx Corporation, Atlanta, Ga.

This example shows the effect of CRL-1095 on Rhodamine 123 (P-gp substrate) accumulation in MDR KB 8-5-11 cells in vitro.

Figure 2:
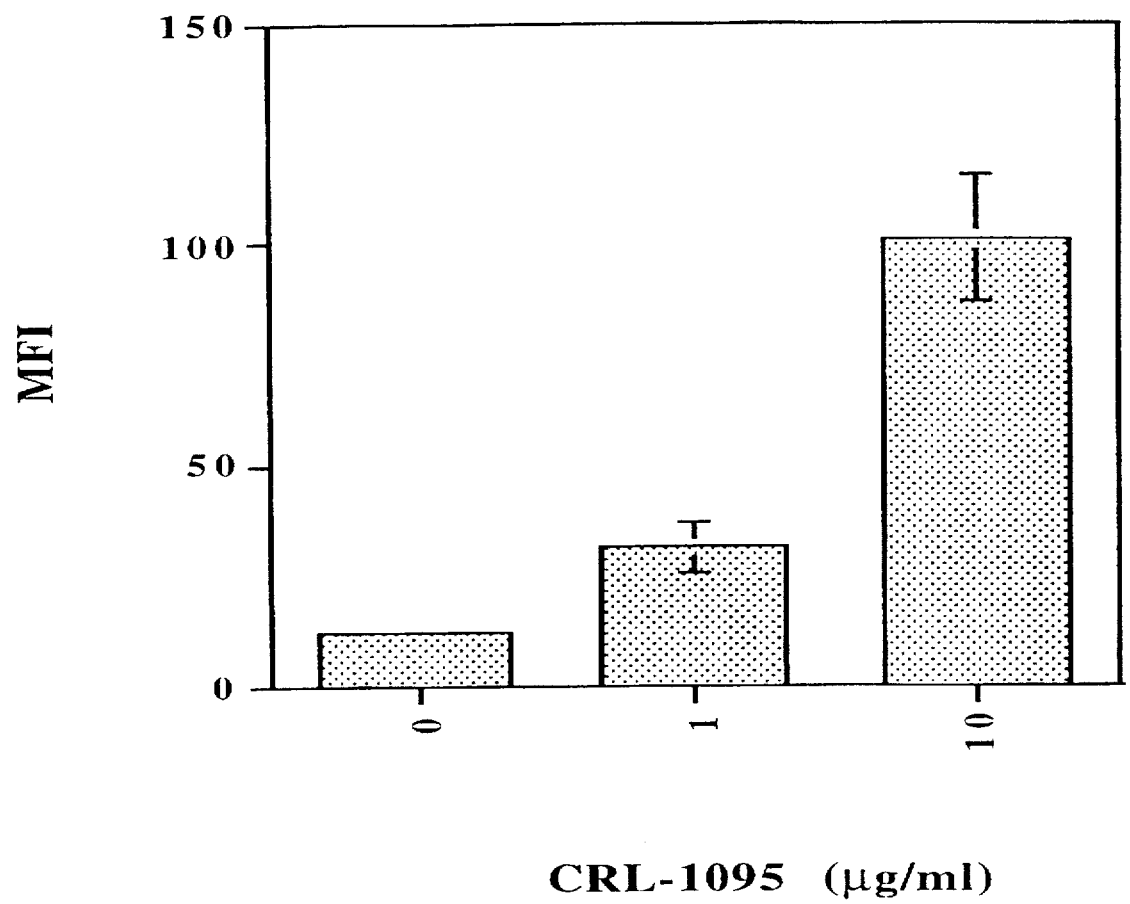
FIG. 2 shows the effect of CRL-1095 on Rhodamine 123 (P-gp substrate) accumulation in MDR KB 8-5-11 cells (In Vitro).

The cell suspension in DMEM ($5 \times 10^5$/ml) is incubated with 0.5 μg/ml of Rhodamine 123 and indicated concentrations of CRL-1095. After incubation for 60 min. at 37° C., the cell suspension was pelleted and washed in cold DMEM for immediate flow cytometric analysis (See Example III). The term "MFI" means "mean fluorescence intensity" resulting from intracellular Rhodamine-123. FIG. 2 shows that CRL-1095 enhances the uptake and accumulation of Rhodamine 123 within KB 8-5-11(resistant) epidermal carcinoma cells in a dose dependent manner.

EXAMPLE XI

Figure 3:
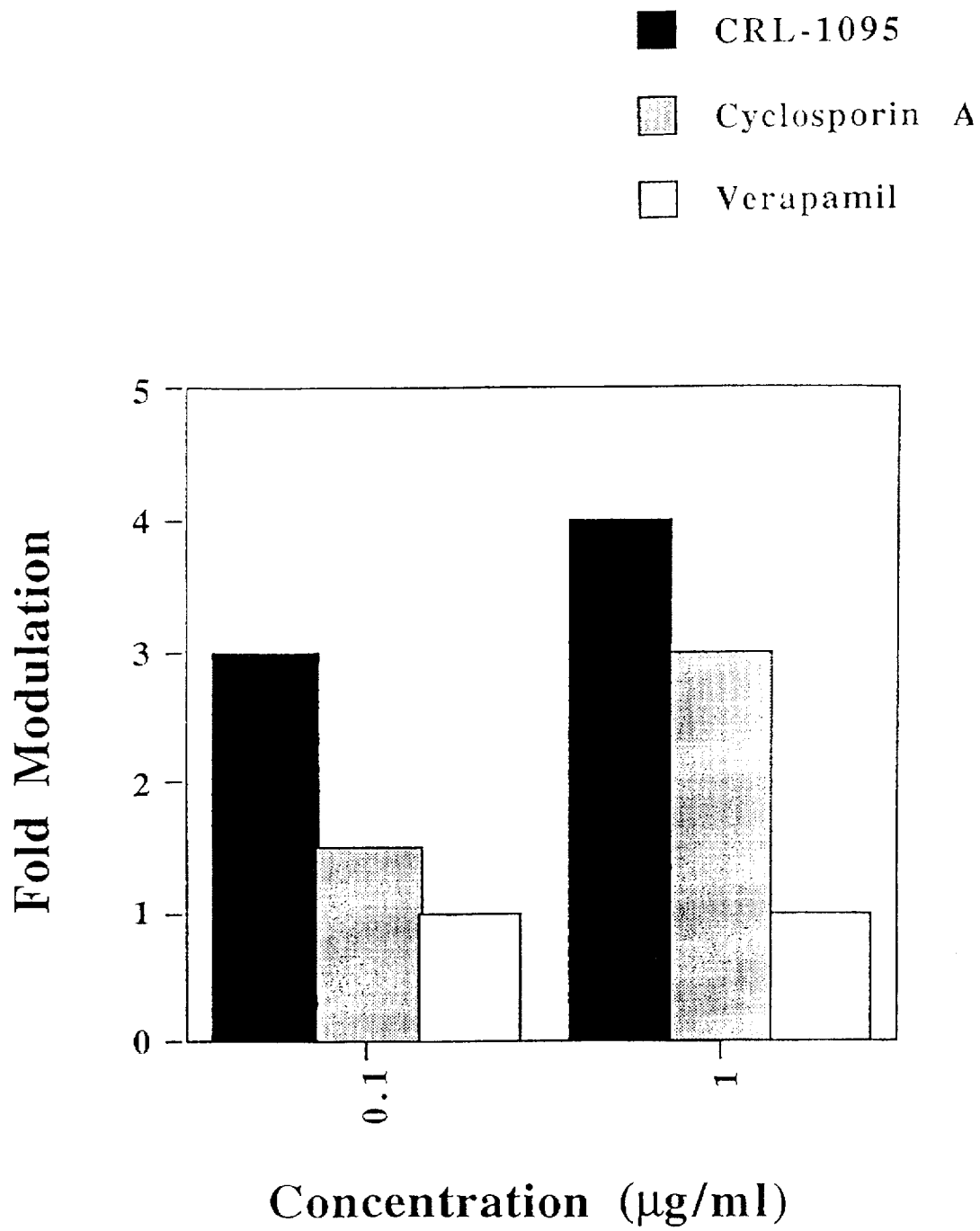
FIG. 3 shows the effect of CRL-1095 on modulation of colchicine resistance on MDR KB 8-5 cells in vitro.

This example shows the effect of CRL-1095 on modulation of colchicine resistance on MDR KB 8-5 cells in vitro. $5 \times 10^5$ cells/well were plated in the presence or absence of modulating agent in combination with colchicine, and incubated for 96 hours. "Fold Modulation" is equal to $IC_{50}$ of drug alone/$IC_{50}$ of drug with resistance modifying agent (RMA). FIG. 3 shows that CRL-1095 modulates colchicine resistance in a dose dependent manner and CRL-1095 exhibits greater effective modulatory activity than either cyclosporine or verapamil at equal concentrations

EXAMPLE XII

Figure 4:
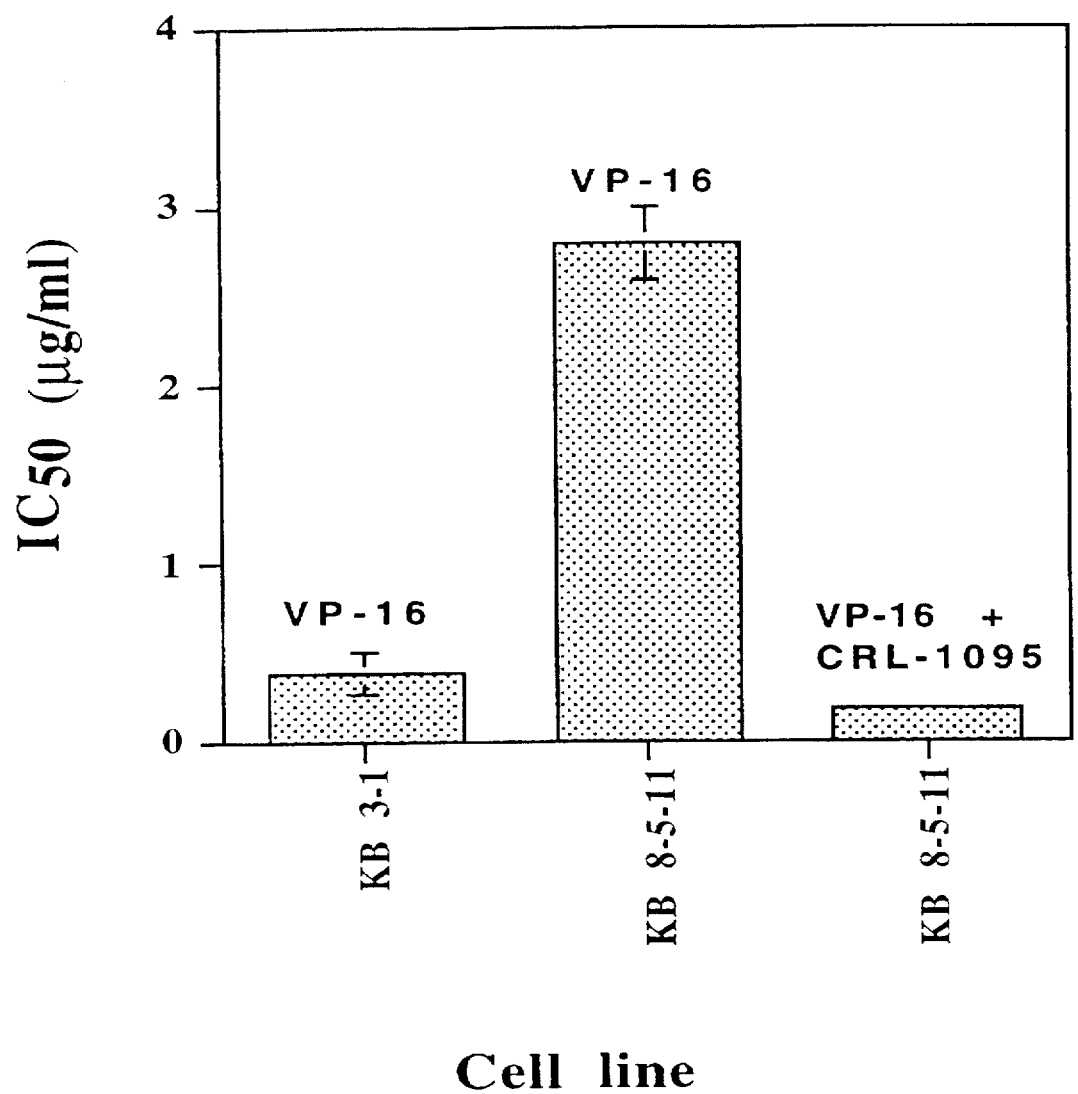
FIG. 4 shows the effect of CRL-1095 on modulation of VP-16 resistance on MDR KB 8-5-11 cells in vitro.

This example shows the effect of CRL-1095 on modulation of VP-16 resistance on MDR KB 8-5-11 cells in vitro. $5 \times 10^3$ cells/well were plated in the presence or absence of CRL-1095 in combination with VP-16 and incubated for 96 hours. $IC_{50}$ is equal to the drug concentration that reduces cell proliferation to 50% of untreated controls using standard MTT cell proliferation assay. FIG. 4 shows that in KB 8-5-11 cells (resistant), CRL-1095 (1 μg/ml) completely reverses VP-16 resistance to levels similar in KB 3-1 (sensitive) cells.

EXAMPLE XIII

Figure 5:
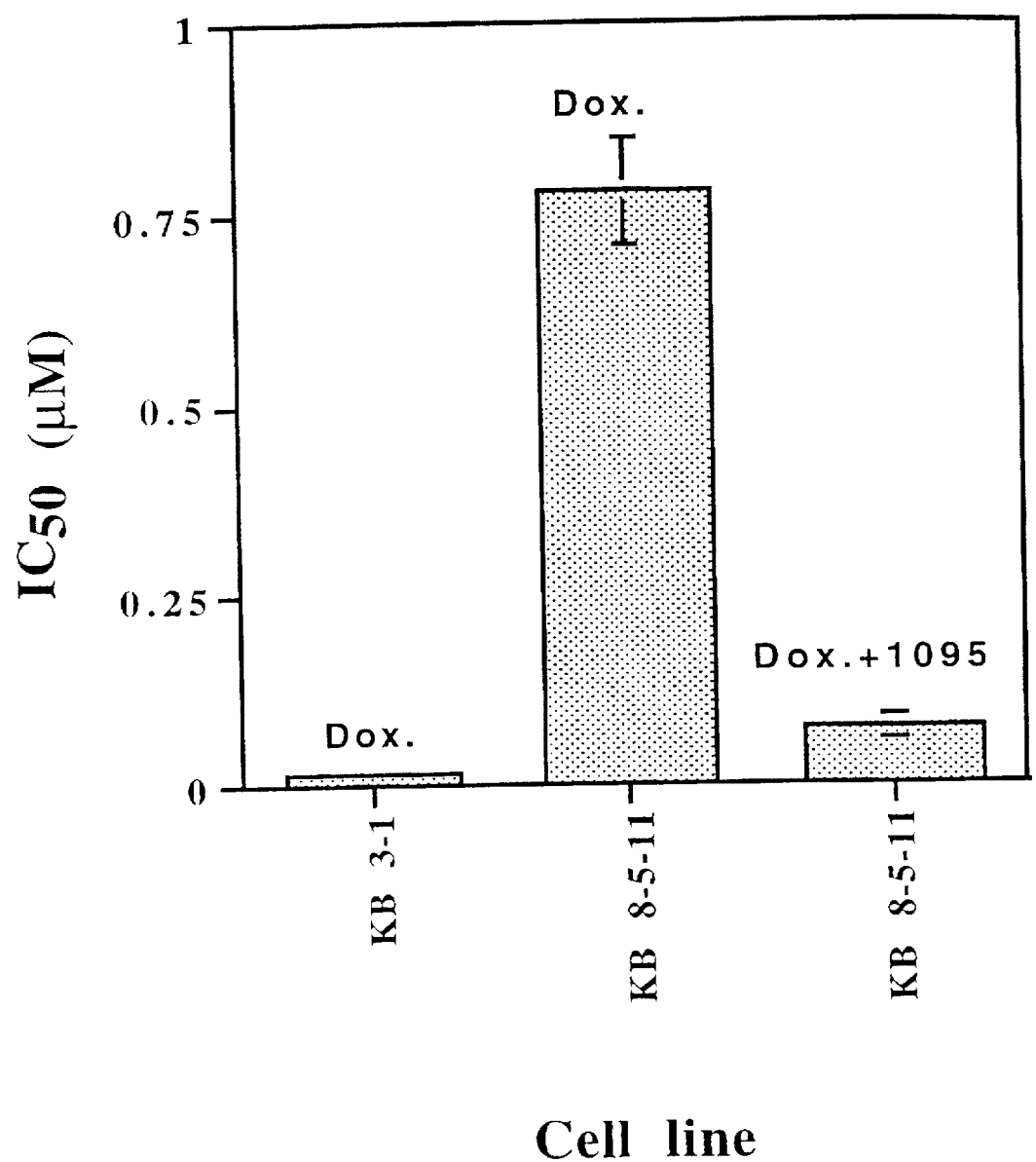
FIG. 5 shows the effect of CRL-1095 on modulation of doxofubicin resistance on MDR KB 8-5-11 cells in vitro.

This example shows the effect of CRL-1095 on modulation of doxorubicin resistance on MDR KB 8-5-11 cells in vitro. $5 \times 10^3$ cells/well were plated in the presence or absence of CRL-1095 in combination with Doxorubicin and incubated for 96 hours. $IC_{50}$ is equal to the drug concentration that reduces cell proliferation to 50% of untreated controls using standard MTT cell proliferation assay. FIG. 5 shows the $IC_{50}$ of doxorubicin (dox.) in KB 8-5-11 (resistant) cells in the presence of CRL-1095 (1 μg/ml) is similar to that in KB 3-1 (sensitive) cells.

EXAMPLE XIV

Figure 6:
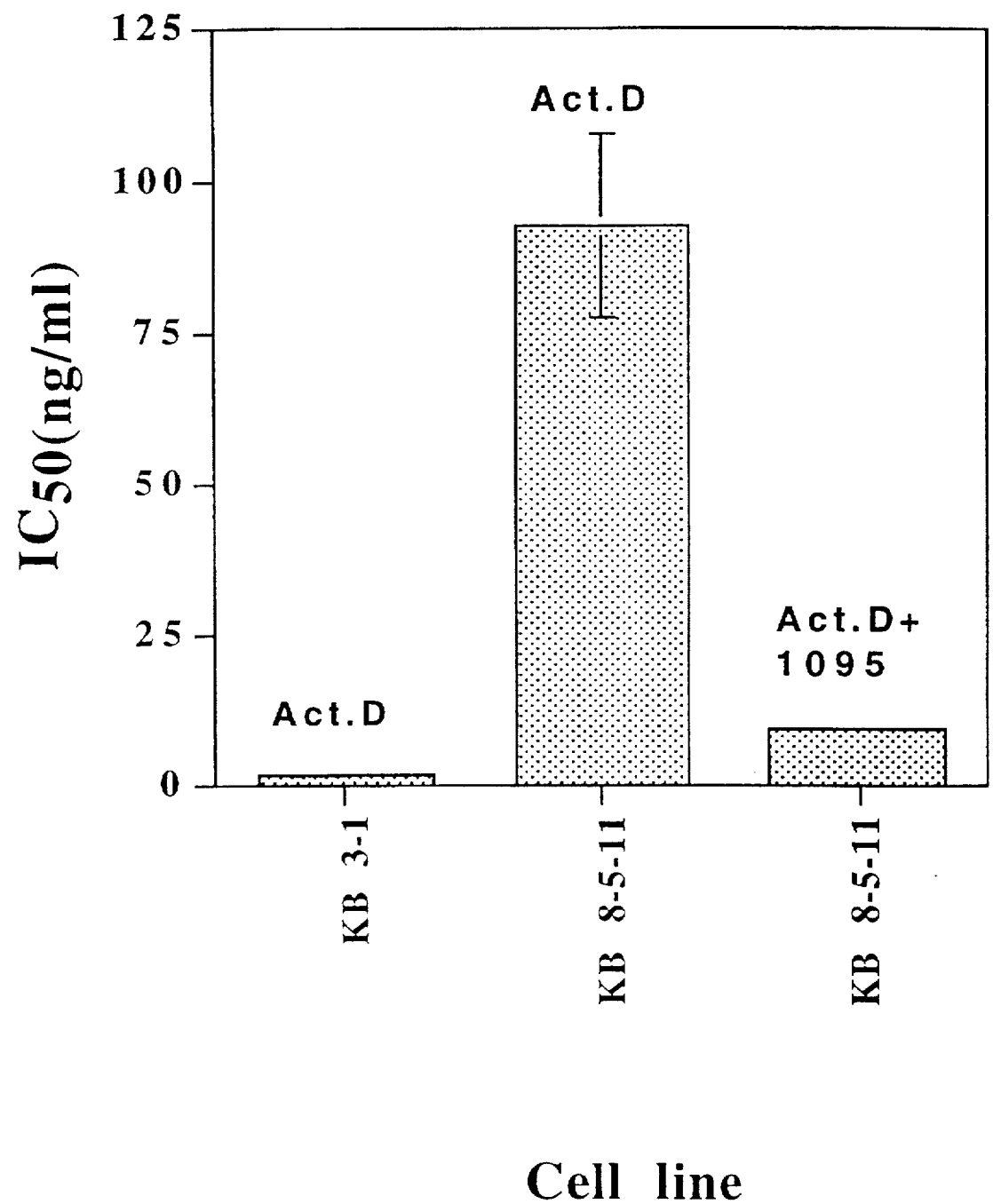
FIG. 6 shows effect of CRL-1095 on modulation of actinomycin resistance on MDR KB 8-5-11 cells in vitro.

This example shows the effect of CRL-1095 on modulation of actinomycin resistance on MDR KB 8-5-11 cells in vitro. $5 \times 10^3$ cells/well were plated in the presence or absence of CRL-1095 in combination with actinomycin and incubated for 96 hours. $IC_{50}$ is equal to the drug concentration that reduces cell proliferation to 50% of untreated controls using standard MTT cell proliferation assay. FIG. 6 shows the $IC_{50}$ of actinomycin D (Act.D) in KB 8-5-11 (resistant) cells in the presence of CRL-1095 (1 μg/ml) is similar to that in KB 3-1 (sensitive) cells.

EXAMPLE XV

Figure 7:
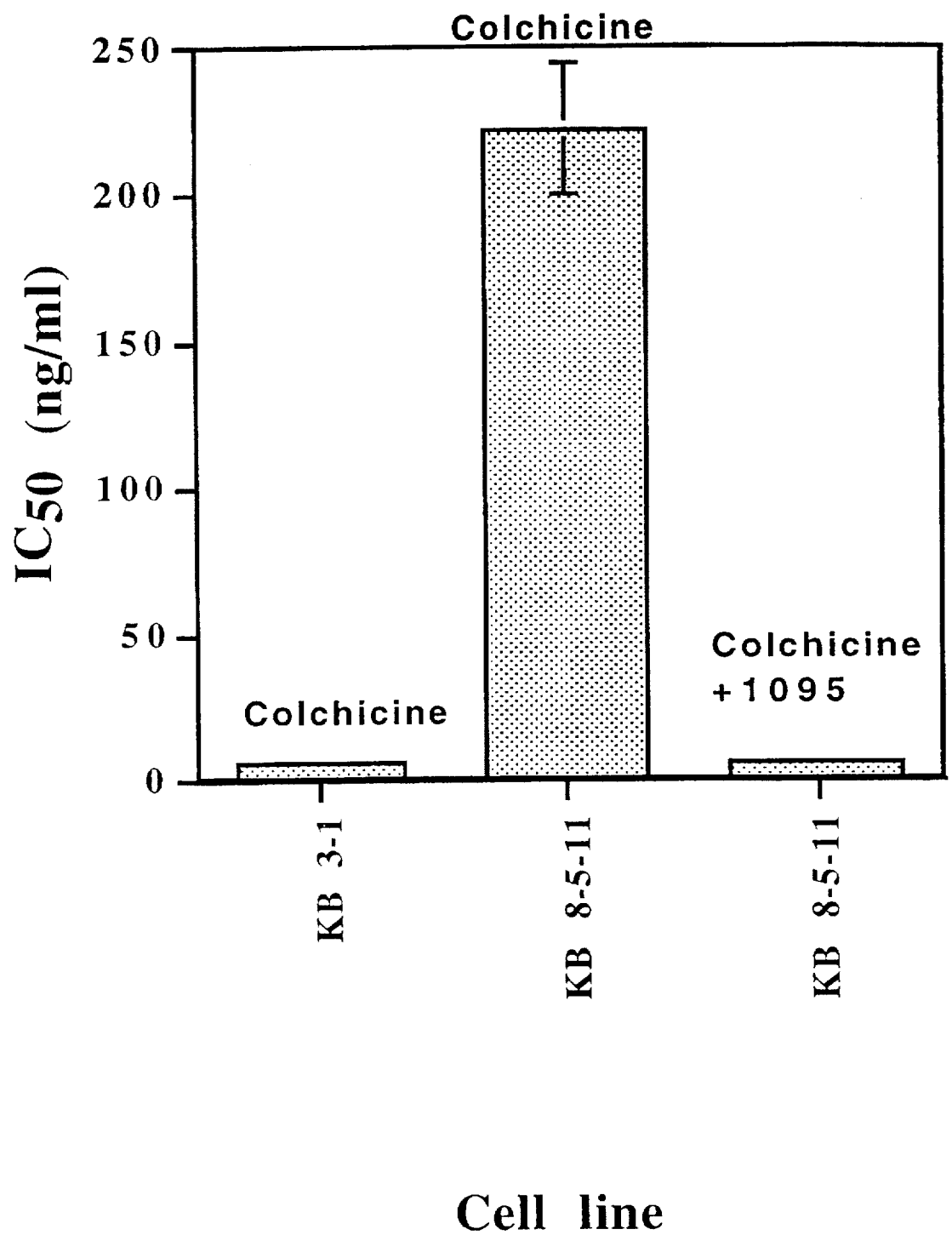
FIG. 7 shows the effect of CRL-1095 on modulation of colchicine resistance on MDR KB 8-5-11 cells in vitro.

This example shows the effect of CRL-1095 on modulation of colchicine resistance on MDR KB 8-5-11 cells in vitro. $5 \times 10^3$ cells/well were plated in the presence or absence of CRL-1095 in combination with colchicine and incubated for 96 hours. $IC_{50}$ is equal to the drug concentration that reduces cell proliferation to 50% of untreated controls using the standard MTT cell proliferation assay. FIG. 7 whows that the $IC_{50}$ of Colchicine in KB 8-5-11 (resistant) cells in the presence of CRL-1095 (1 μg/ml) is similar to that in KB 3-1 (sensitive) cells.

EXAMPLE XVI

Figure 8:
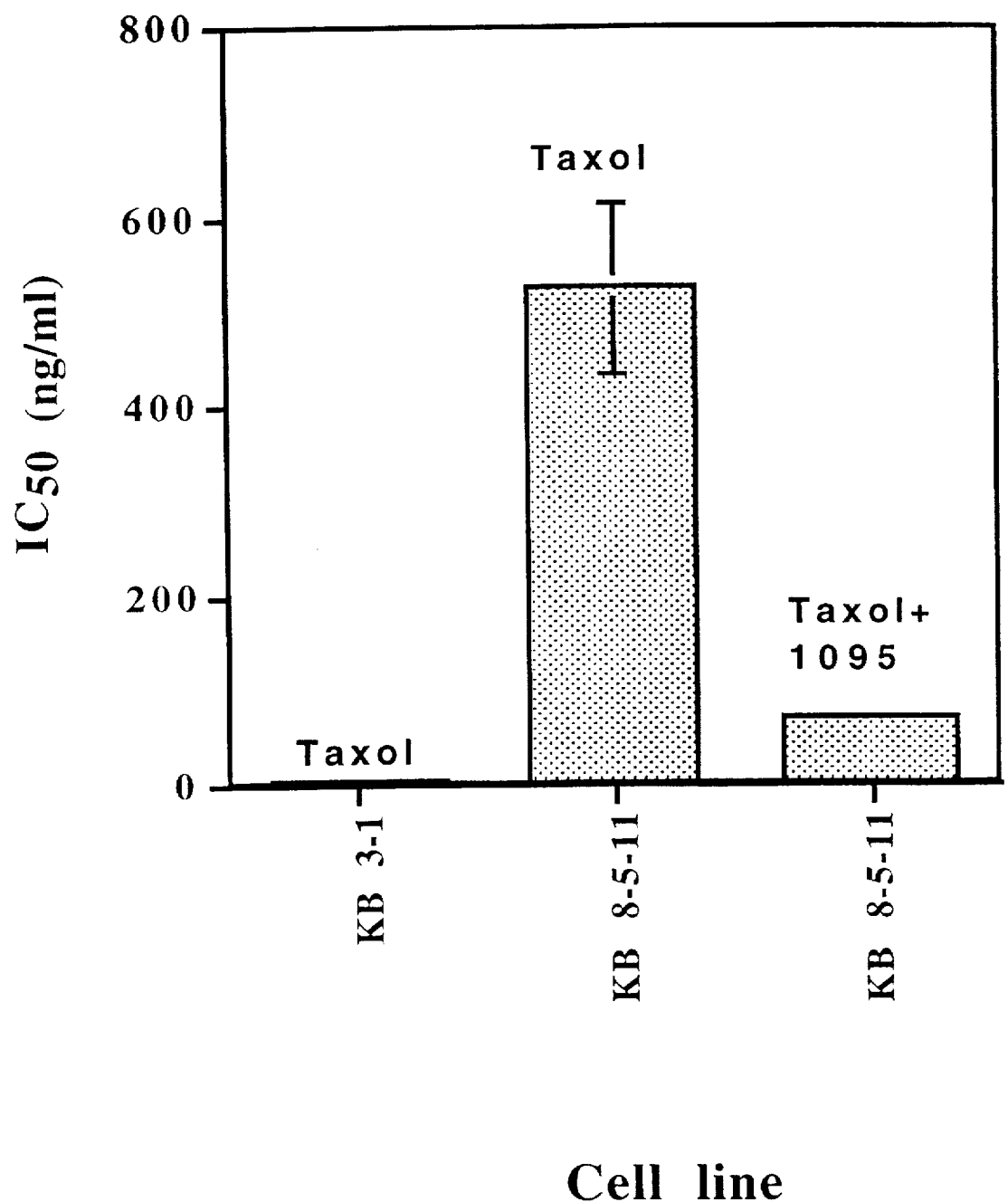
FIG. 8 shows the effect of CRL-1095 on modulation of Taxol resistance on MDR KB 8-5-11 cells in vitro.

This example shows the effect of CRL-1095 on modulation of Taxol resistance on MDR KB 8-5-11 Cells in vitro. $5 \times 10^3$ cells/well were plated in the presence or absence of CRL-1095 in combination with Taxol and incubated for 72 h. $IC_{50}$ is equal to the drug concentration that reduces cell proliferation to 50% of untreated controls using standard MTT cell proliferation assay. FIG. 8 shows the $IC_{50}$ of Taxol in KB 8-5-11 (resistant) cells in the presence of CRL-1095 (1 μg/ml) is 5–6-fold reduced.

EXAMPLE XVII

Figure 9:
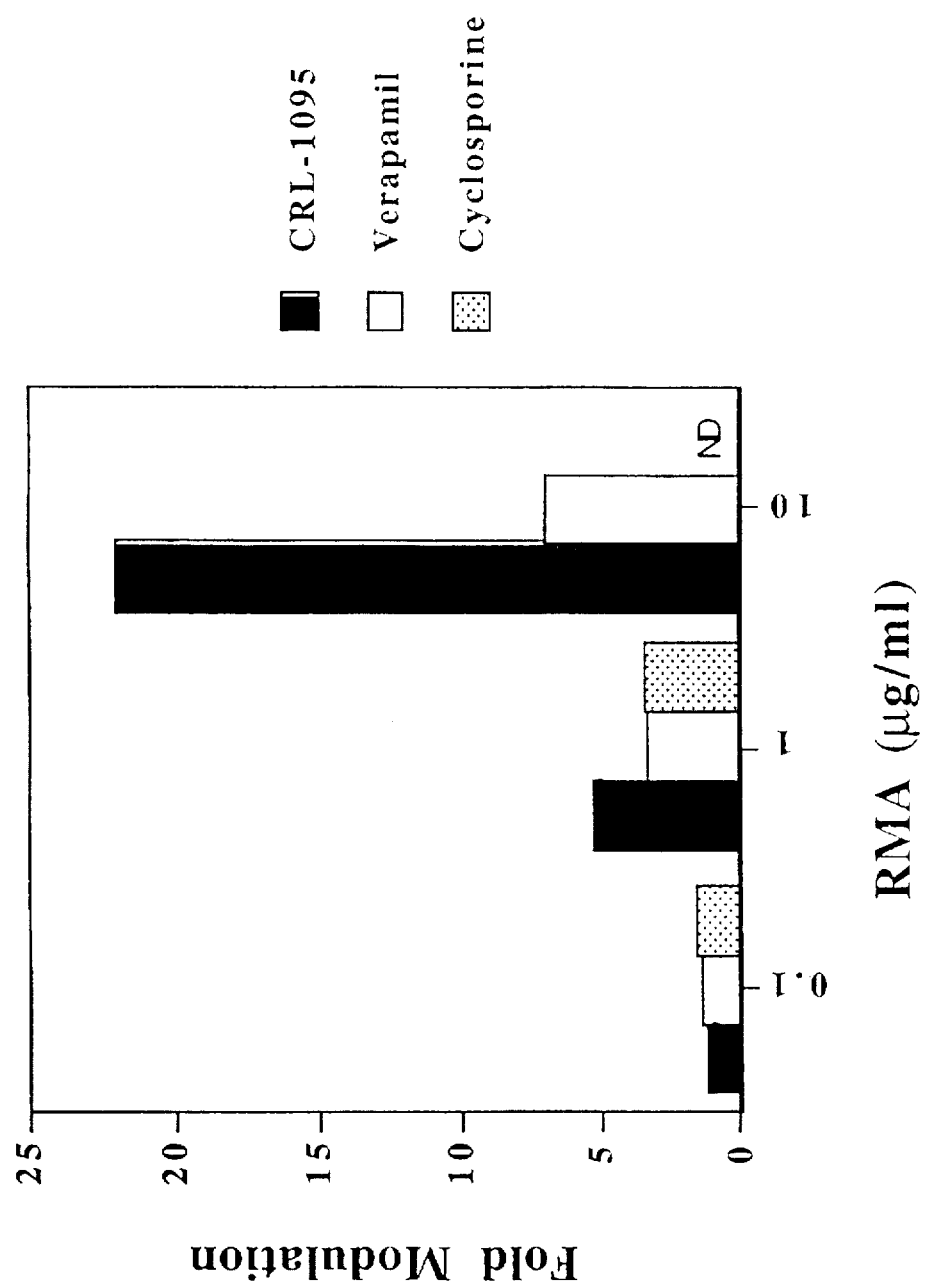
FIG. 9 shows the effect of CRL-1095 on modulation of daunonibicin resistance in MDR erythro-leukemic K562/III cells.

This example shows the effect of CRL-1095 on modulation of daunorubicin resistance in MDR erythro-leukemic K562/III cells. $5 \times 10^3$ K562/III erythro-leukemic cells/well were plated in the presence or absence of CRL-1095 plus increasing amounts of daunorubicin, and incubated for 72 h. "Fold modulation" is equal to $IC_{50}$ of drug alone/$IC_{50}$ of drug with modulator. $IC_{50}$ is equal to the drug concentration that reduces cell proliferation to 50% of untreated controls using standard MTT cell proliferation assay. Cyclosporine was cytotoxic at 10 μg/ml, and fold modulation was not determined (ND). FIG. 9 shows the CRL-1095 effectively modulates Daunorubicin resistance in a dose-dependent manner. In addition, CRL-1095 exhibits a 4-fold higher modulatory effect than verapamil at 10 µg/ml. At similar doses (1 µg/ml) modulation by CRL-1095 is more effective than verapamil and cyclosporine.

EXAMPLE XVIII

Figure 10:
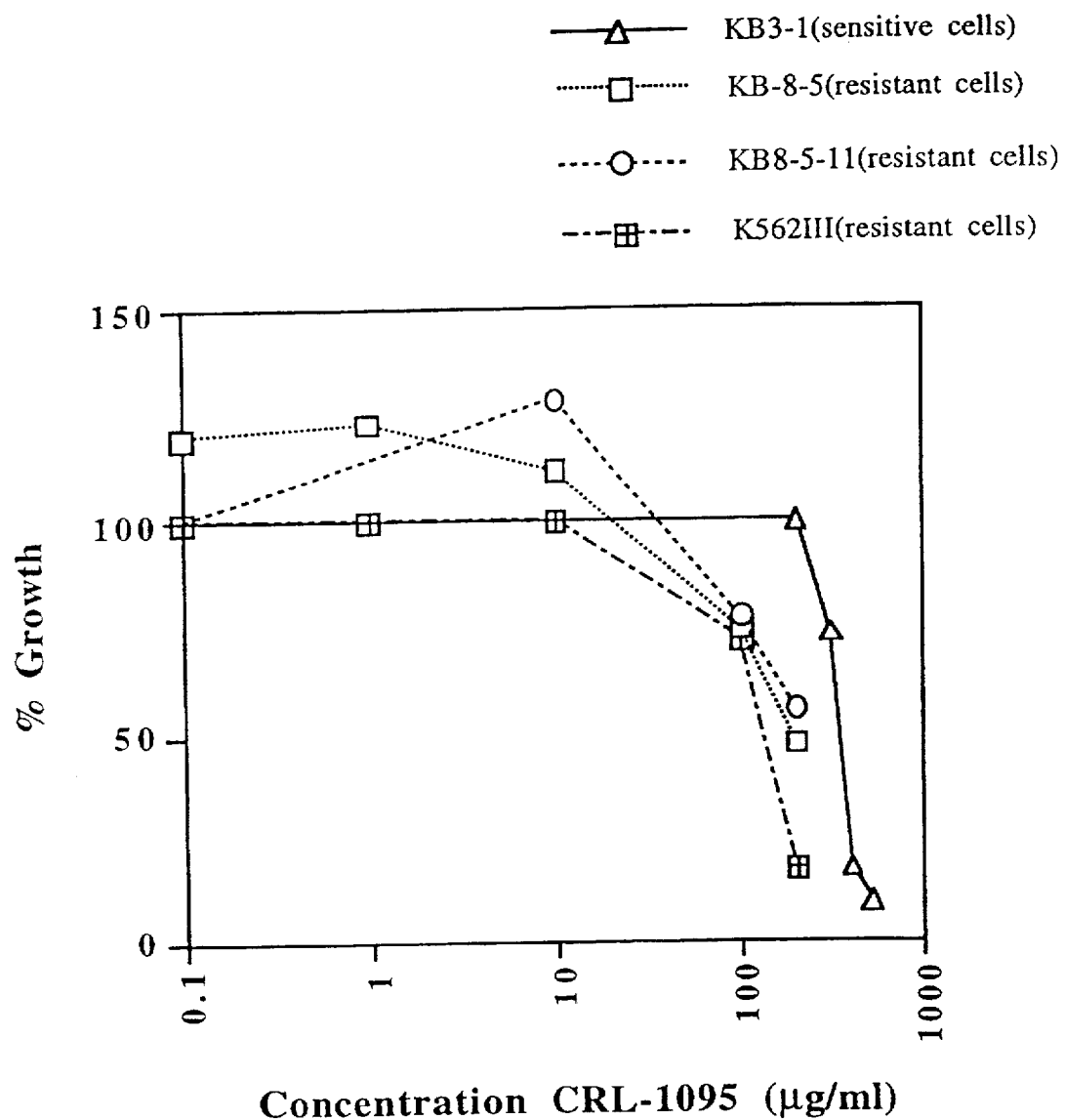
FIG. 10 shows the cytotoxicity of CRL-1095 on KB 3-1, KB 8-5, KB 8-5-11, and K562/III cells.
Figure 11:
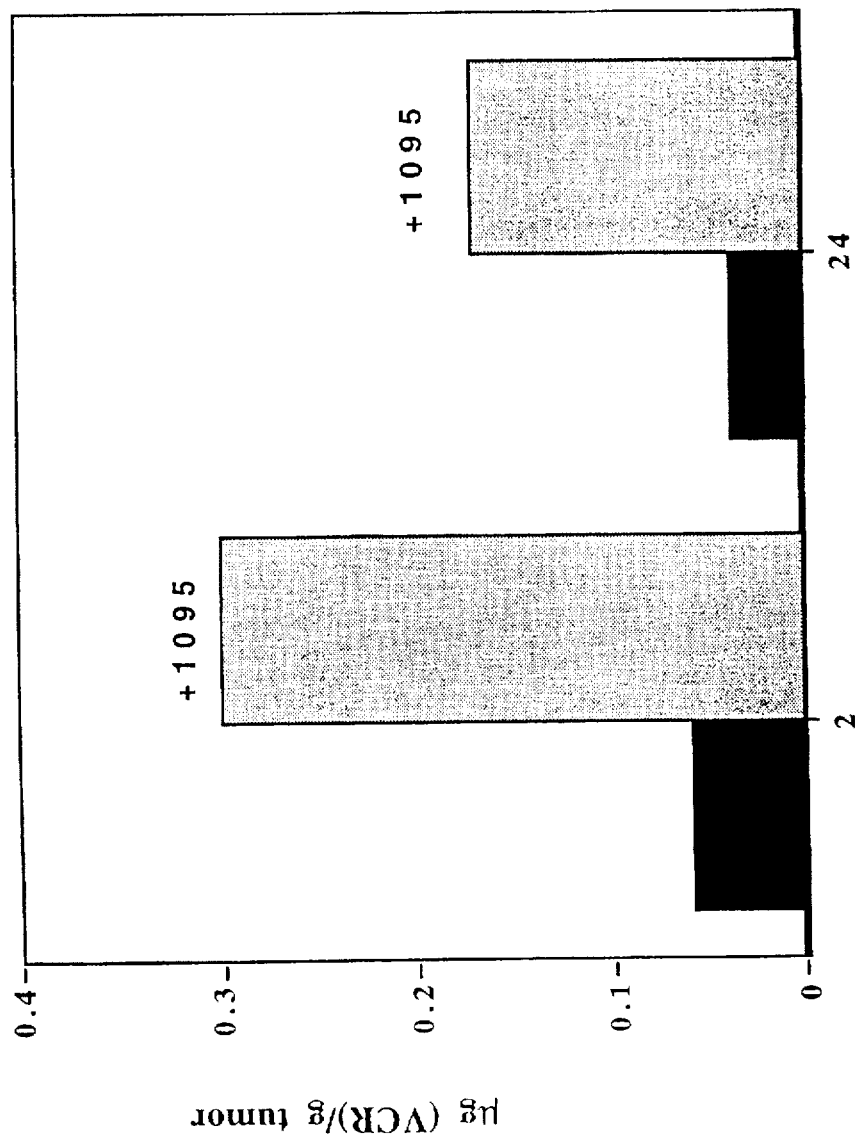
FIG. 11 shows the effect of CRL-1095 on vincristine accumulation in KB 8-5 human xenograft tumor tissue in mice.

This example shows the cytotoxicity of CRL-1095 on KB 3-1, KB 8-5, KB 8-5-11, and K562/III cells. As shown in FIG. 10, cells are treated with increasing concentrations of CRL-1095 for 72 h. $IC_{50}$ is equal to the drug concentration that reduces cell proliferation to 50% of untreated controls using standard MTT cell proliferation assay. Growth is related as % relative to untreated cells. As shown in FIG. 10, CRL-1095 is tolerated at relatively high doses in vitro. A comparison of $CC_{50}$ levels for parental and drug resistant tumor cell lines is shown in Table VI. CRL-1095 is 4–19 times less cytotoxic than verapamil or cyclosporine.

TABLE VI

| Cell Line | $CC_{50}$ (µg/ml) | | |
|---|---|---|---|
| | CRL-1095 | Verapamil | Cyclosporine |
| KB3-1 | 340 | 40 | 50 |
| KB8-5 | 190 | 10 | ND |
| KB8-5-11 | >200 | 27 | 42 |
| K562/III | 140 | 38 | 22 |

EXAMPLE XIX

This example shows the acute toxicity of CRL-1095 in C57B1/6 mice. C57B1/6 mice were administered via intravenous route a bolus injection at concentrations indicated in Table VII, or with vehicle control. Survival was monitored through 14 days post injection. As seen in Table VII, in vivo studies in C57B1/6 mice indicate that CRL-1095 is tolerated at relatively high doses. Maximum tolerated dose (MTD) of CRL-1095 in which all mice survived is 500 mg/kg. MTD of Verapamil is 75 mg/kg (Horton, et al., 1989) and Cyclosporine is 30 mg/Kg (personnel communication with Dr. plowman at NCI).

TABLE VII

| Dose (mg/kg) RMA | Survival CRL-1095 |
|---|---|
| 0 | 5/5 |
| 100 | 5/5 |
| 200 | 5/5 |
| 300 | 5/5 |
| 400 | 5/5 |
| 500 | 5/5 |
| 640 | 0/5 |

EXAMPLE XX

Figure 12:
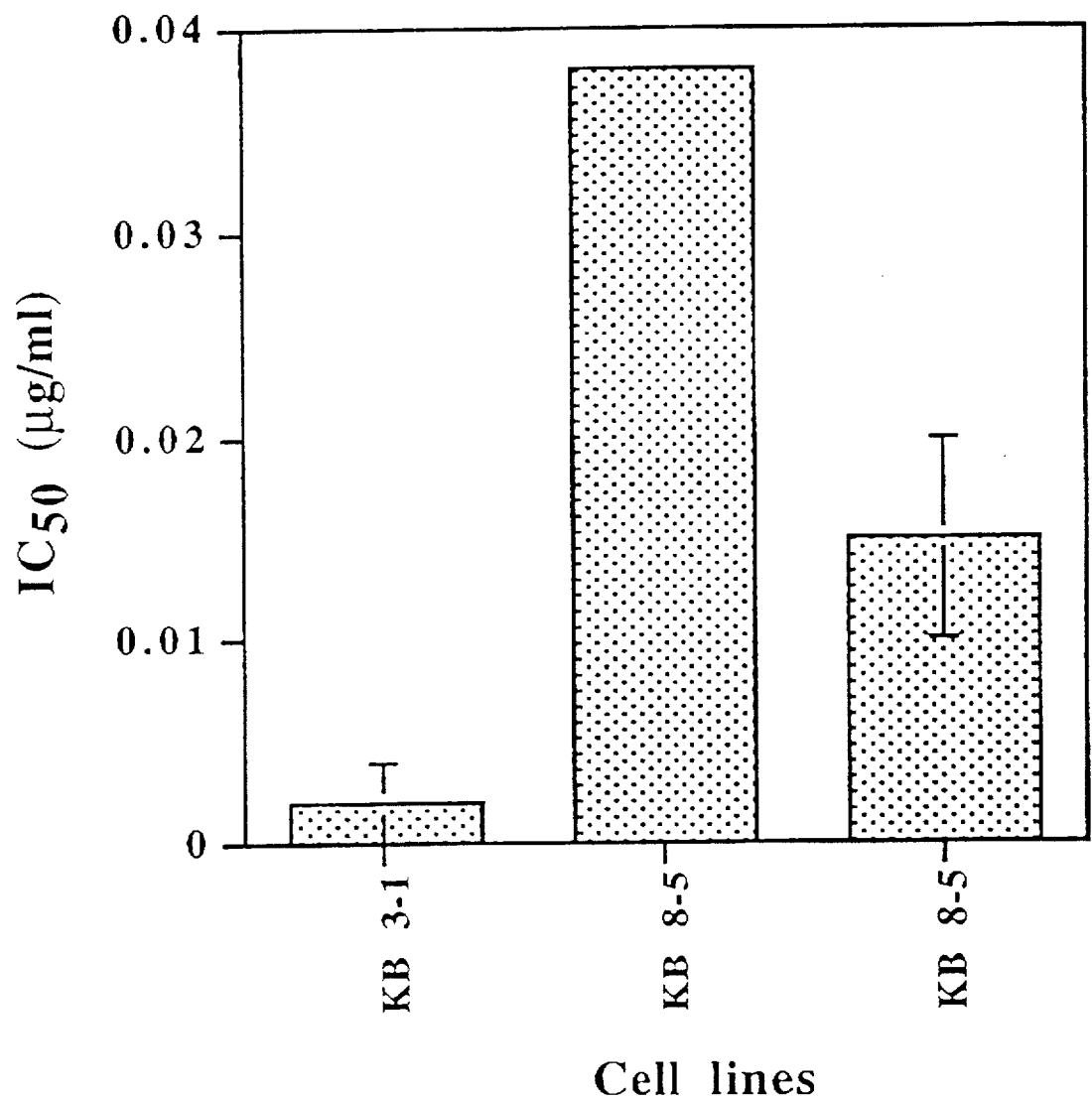
FIG. 12 shows the effect of CRL-1605 on modulation of Taxol resistance on MDR KB 8-5 cells.

This example shows the effect of CRL-1095 on vincristine accumulation in KCB 8-5 human xenograft tumor tissue in mice. Nude mice carrying the human xenograft tumor, KB 8-5, were given $^3$H-Vincristine (VCR) (2 mg/kg, i.p.) as a single injection with or without CRL-1095 (50 mg/kg, i.v.). At various time points following drug administration, tissues were removed and counted for radioactivity. FIG. 12 shows that intravenous (IV) administration of CRL-1095 increases accumulation of $^3$H-Vincristine 4–6 fold in human xenograft tumor tissue in mice.

EXAMPLE XXI

Examples XXI through XXV are directed to CRL-1605. This molecule has the following structure:

$HO(C_3H_6O)_a(C_2H_4O)_b(C_3H_6O)_aH$ wherein the average of "a" is approximately 40 and "b" is approximately 20 and is designated CRL 1605. This molecule is available from CytRx Corporation, Atlanta, Ga.

In a 2 liter stainless steel pressure reactor, 3.7 grams of dry cesium hydroxide monohydrate and 14.5 grams of ethyle glycol are mixed and the reactor is evacuated. The contents are heated at 100° C. and 200 grams of ethylene oxide is slowly allowed to react to produce a polyethylene glycol polymer of molecular eight of about 875 daltons. 1084 grams of propylene oxide then is slowly allowed to react with the contents in the reactor to produce a block copolymer with a molecular weight of about 5040 daltons. The contents are heated with 18.4 grams of magnesium silicate and 1.8 grams of silica at 100° C. for 6 hours to adsorb the catalyst. The block copolymer product is isolated by filtration. The final product has a cloud point of 11.3° C.

This example shows the effect of the CRL-1605 on modulation of Taxol resistance on MDR KB 8-5 cells. $5 \times 10^3$ cells/ml were plated in the presence or absence of CRL-1605 in combination with Taxol and incubated for 72 h. FIG. 12 shows the $IC_{50}$ of Taxol in KB 8-5 (R) cells is 2-fold reduced in the presence of CRL-1605 (1 µg/ml).

EXAMPLE XXII

Figure 13:
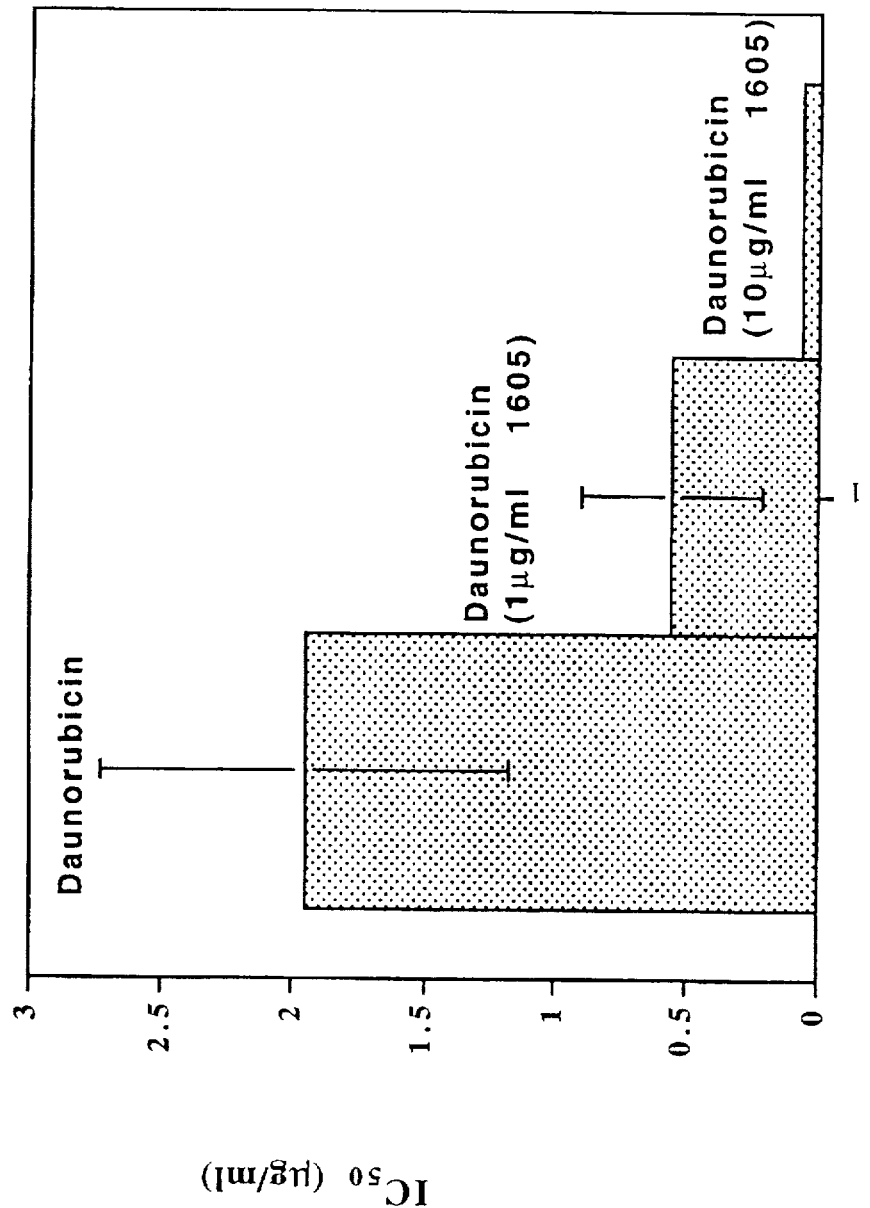
FIG. 13 shows the effect of CRL-1605 on modulation of daunorubicin resistance on MDR K562/III cells.

This example shows the effect of CRL-1605 on modulation of daunorubicin resistance on MDR K562/III cells. $5 \times 10^3$ cells/ml were plated in the presence or absence of CRL-1605 in combination with Daunorubicin and incubated for 72 h. FIG. 13 shows the $IC_{50}$ of Daunorubicin in K562/III (R) is 40-fold reduced in the presence of CRL-1605 (10 µg/ml).

EXAMPLE XXIII

Figure 14:
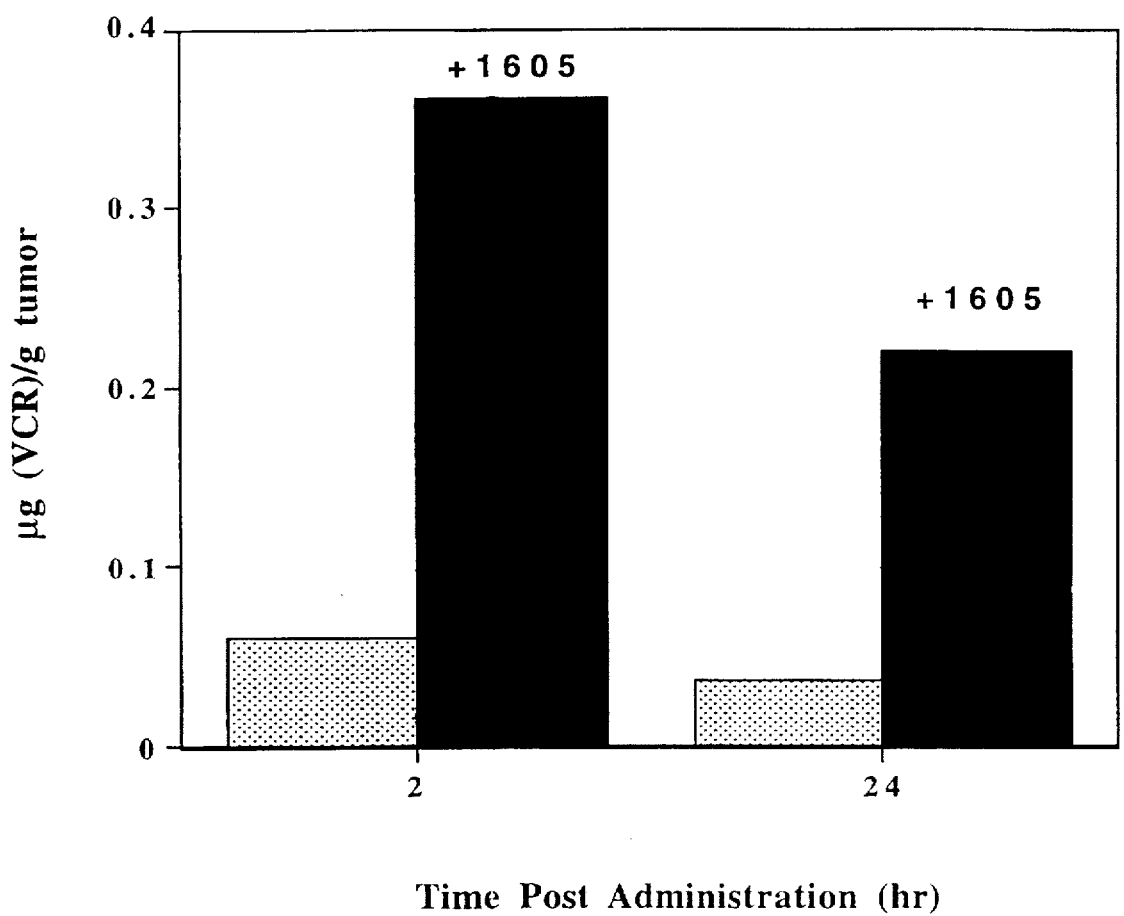
FIG. 14 shows the effect of CRL-1605 on vincristine accumulation in KB 8-5 human xenograft tumor tissue in mice.
Figure 15:
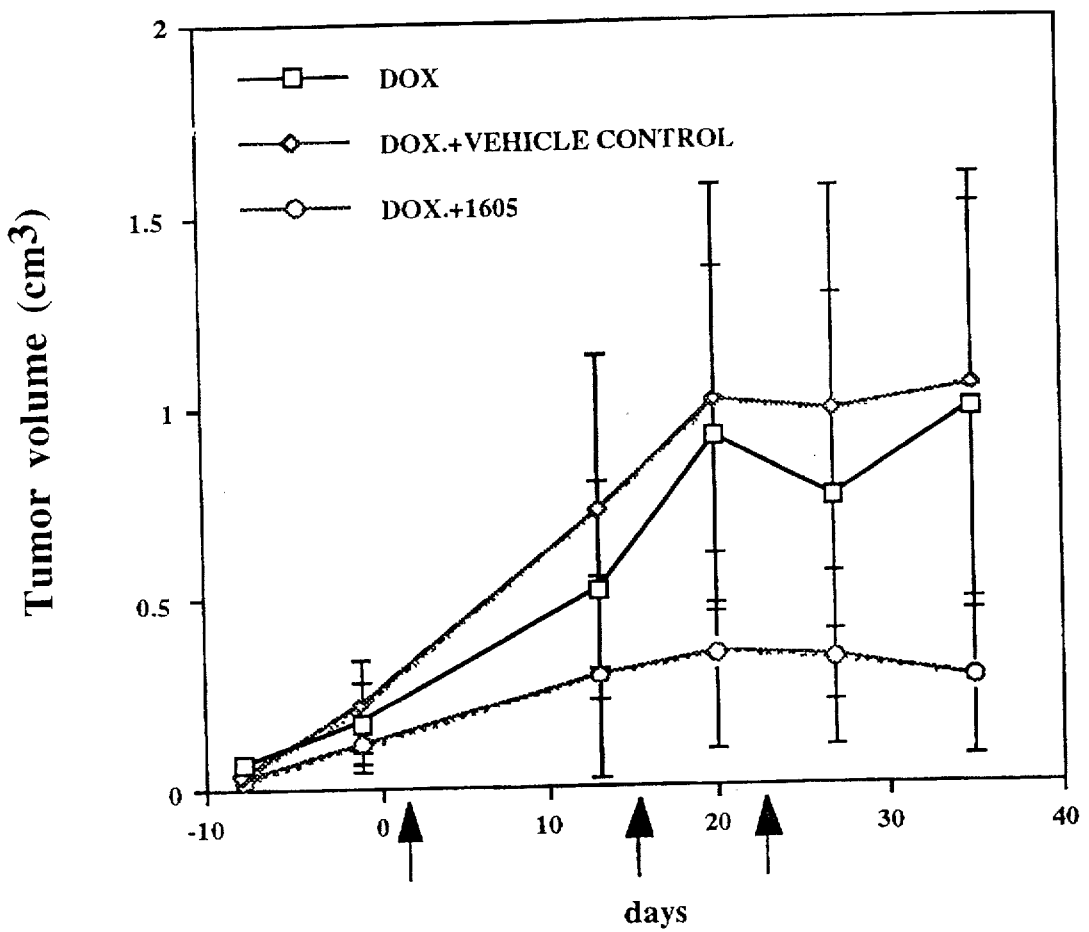
FIG. 15 shows the modulation of tumor growth in KB 8-5 human xenograft model by CRL-1605.

This example shows the effect of CRL-1605 on vincristine accumulation in KB 8-5 human xenograft tumor tissue in mice. Nude mice carrying the human xenograft tumor, KB 8-5, were given $^3$H-Vincristine (VCR) (2 mg/kg, i.p.) as a single injection with or without CRL-1605 (50 mg/kg, i.v.). At various time points following drug administration, tissues were removed and counted for radioactivity. FIG. 14 shows that the intravenous (IV) administration of CRL-1605 increases accumulation of $^3$H-Vincristine 4–6 fold in human xenograft tumor tissue in mice.

EXAMPLE XXIV

This example shows the acute toxicity of CRL-1605 in C57B1/6 mice. In vivo studies in C57B1/6 mice indicate that CRL-1605 is tolerated at relatively high doses. As shown in Table VIII, the maximum tolerated dose (MTD) of CRL-1605 is 350 mg/kg. At 400 mg/Kg mice were slightly ill. MTD of Verapamil is 75 mg/kg (Horton, et al., 1989) and the MTD of cyclosporine is 30 mg/Kg (personnel communication with Dr. Plowman at National Cancer Institute).

TABLE VIII

| Dose (mg/kg) | Survival |
| RMA | CRL-1095 |
| --- | --- |
| 0 | 5/5 |
| 100 | 5/5 |
| 200 | 5/5 |
| 300 | 4/5 |
| 400 | 3/7 |
| 500 | 0/5 |
| 640 | 0/5 |

EXAMPLE XXV

This example shows the modulation of tumor growth in KB 8-5 human xenograft model by CRL-1605. Human KB 8-5 tumors (2 mm$^3$) were implanted on both sides of the hind flank in nude mice (strain NCR/Nu/NCI). Two weeks following implantation, treatment was administered on days 1, 5, and 23 as follows: Doxorubicin only animals received doxorubicin 8 mg/kg. Doxorubicin+vehicle animals received the same dose of doxorubicin plus the equivalent volume of CRL-1605 vehicle. Doxorubicin+CRL-1605 animals received the same dose of doxorubicin plus a total daily dose of 100 mg/kg CRL-1605 administered as 4 individual doses of 25 mg/kg at 2 hour intervals. Tumor volume was measured electronically using calipers. Each point represents the average of 4–8 tumors.

It should be understood, of course, that the foregoing relates only to a preferred embodiment of the present invention and that numerous modifications or alterations may be made therein without departing from the spirit and the scope of the invention as set forth in the appended claims.

What is claimed is:

1. A composition for reversing multidrug resistance comprising:

$$HO(C_3H_6O)_a(C_2H_4O)_b(C_3H_6O)_aH$$

wherein "a" is between approximately 20 through 60 and "b" is between approximately 10 and 30, and a chemotherapeutic agent.

2. The composition of claim 1 wherein "a" is between approximately 30 and 50 and "b" is between approximately 15 and 25.

3. The composition of claim 1 where "a" is approximately 40 and "b" is approximately 20.

* * * * *